(12) United States Patent
Cramer et al.

(10) Patent No.: US 12,734,019 B2
(45) Date of Patent: Sep. 15, 2026

(54) PHOTO-BASED DENTAL ATTACHMENT DETECTION

(71) Applicant: ALIGN TECHNOLOGY, INC., San Jose, CA (US)

(72) Inventors: Christopher E. Cramer, Durham, NC (US); Chad Clayton Brown, Cary, NC (US); Guotu Li, Apex, NC (US)

(73) Assignee: Align Technology, Inc., San Jose, CA (US)

( * ) Notice: Subject to any disclaimer, the term of this patent is extended or adjusted under 35 U.S.C. 154(b) by 714 days.

(21) Appl. No.: 18/157,067

(22) Filed: Jan. 19, 2023

(65) Prior Publication Data

US 2023/0225832 A1 Jul. 20, 2023

Related U.S. Application Data

(60) Provisional application No. 63/301,412, filed on Jan. 20, 2022.

(51) Int. Cl.

| | |
|---|---|
| ***G16H 20/40*** | (2018.01) |
| ***A61C 7/00*** | (2006.01) |
| ***A61C 7/08*** | (2006.01) |
| ***A61C 7/14*** | (2006.01) |
| ***G06T 7/00*** | (2017.01) |

(Continued)

(52) U.S. Cl.

CPC ................ *A61C 7/002* (2013.01); *A61C 7/08* (2013.01); *A61C 7/146* (2013.01); *G06T 7/0012* (2013.01); *G06T 7/12* (2017.01); *G06T 7/62* (2017.01); *G16H 10/60* (2018.01); *G16H 20/40* (2018.01); *G06T 2207/30036* (2013.01)

(58) Field of Classification Search

CPC ........... A61C 7/002; A61C 7/08; A61C 7/146; A61C 7/00; G06T 7/62; G06T 7/12; G06T 7/0012; G06T 2207/30036; G16H 20/40; G16H 10/60

USPC .......................................................... 382/128

See application file for complete search history.

(56) References Cited

U.S. PATENT DOCUMENTS

| | | | |
|---|---|---|---|
| 5,975,893 | A | 11/1999 | Chishti et al. |
| 6,227,850 | B1 | 5/2001 | Chishti et al. |

(Continued)

FOREIGN PATENT DOCUMENTS

| | | | | |
|---|---|---|---|---|
| EP | 3831331 | A1 * | 6/2021 | ............. A61C 7/002 |
| WO | 2021163285 | A1 | 8/2021 | |

OTHER PUBLICATIONS

Mahdi, F.P., Motoki, K. & Kobashi, S. Optimization technique combined with deep learning method for teeth recognition in dental panoramic radiographs. Sci Rep 10, 19261 (2020). https://doi.org/10.1038/s41598-020-75887-9 (Year: 2020).*

(Continued)

*Primary Examiner* — Jennifer Mehmood
*Assistant Examiner* — Eric James Shoemaker
(74) *Attorney, Agent, or Firm* — FisherBroyles, LLP

(57) ABSTRACT

A method for dental treatment may include receiving a plurality of images of a patient's dentition, identifying, from the plurality of images, individual teeth of the patient's dentition, detecting, from the plurality of images, one or more attachments on the patient's dentition, assigning, based on each of the plurality of images, each of the one or more attachments to one of the individual teeth in each image, and combining the assignments of each of the plurality of images for attachment detection results.

23 Claims, 15 Drawing Sheets

(51) Int. Cl.

| | |
|---|---|
| ***G06T 7/12*** | (2017.01) |
| ***G06T 7/62*** | (2017.01) |
| ***G16H 10/60*** | (2018.01) |

(56) References Cited

U.S. PATENT DOCUMENTS 6,227,851 B1 5/2001 Chishti et al.
6,299,440 B1 10/2001 Phan et al.
6,309,215 B1 10/2001 Phan et al.
6,318,994 B1 11/2001 Chishti et al.
6,371,761 B1 4/2002 Cheang et al.
6,386,878 B1 5/2002 Pavlovskaia et al.
6,406,292 B1 6/2002 Chishti et al.
6,409,504 B1 6/2002 Jones et al.
6,450,807 B1 9/2002 Chishti et al.
6,457,972 B1 10/2002 Chishti et al.
6,488,499 B1 12/2002 Miller
6,514,074 B1 2/2003 Chishti et al.
6,554,611 B2 4/2003 Chishti et al.
6,582,229 B1 6/2003 Miller et al.
6,602,070 B2 8/2003 Miller et al.
6,621,491 B1 9/2003 Baumrind et al.
6,688,886 B2 2/2004 Hughes et al.
6,726,478 B1 4/2004 Isiderio et al.
6,729,876 B2 5/2004 Chishti et al.
6,739,869 B1 5/2004 Taub et al.
6,767,208 B2 7/2004 Kaza
6,783,360 B2 8/2004 Chishti
6,830,450 B2 12/2004 Knopp et al.
7,040,896 B2 5/2006 Pavlovskaia et al.
7,063,532 B1 6/2006 Jones et al.
7,074,038 B1 7/2006 Miller
7,074,039 B2 7/2006 Kopelman et al.
7,077,647 B2 7/2006 Choi et al.
7,108,508 B2 9/2006 Hedge et al.
7,134,874 B2 11/2006 Chishti et al.
7,156,661 B2 1/2007 Choi et al.
7,160,107 B2 1/2007 Kopelman et al.
7,241,142 B2 7/2007 Abolfathi et al.
7,293,988 B2 11/2007 Wen
7,309,230 B2 12/2007 Wen
7,357,634 B2 4/2008 Knopp
7,555,403 B2 6/2009 Kopelman et al.
7,637,740 B2 12/2009 Knopp
7,689,398 B2 3/2010 Cheng et al.
7,736,147 B2 6/2010 Kaza et al.
7,746,339 B2 6/2010 Matov et al.
7,844,356 B2 11/2010 Matov et al.
7,844,429 B2 11/2010 Matov et al.
7,865,259 B2 1/2011 Kuo et al.
7,878,804 B2 2/2011 Korytov et al.
7,880,751 B2 2/2011 Kuo et al.
7,904,308 B2 3/2011 Arnone et al.
7,930,189 B2 4/2011 Kuo
7,942,672 B2 5/2011 Kuo
7,970,627 B2 6/2011 Kuo et al.
7,970,628 B2 6/2011 Kuo et al.
8,038,444 B2 10/2011 Kitching et al.
8,044,954 B2 10/2011 Kitching et al.
8,075,306 B2 12/2011 Kitching et al.
8,092,215 B2 1/2012 Stone-Collonge et al.
8,099,268 B2 1/2012 Kitching et al.
8,108,189 B2 1/2012 Chelnokov et al.
8,126,726 B2 2/2012 Matov et al.
8,260,591 B2 9/2012 Kass et al.
8,275,180 B2 9/2012 Kuo
8,401,826 B2 3/2013 Cheng et al.
8,439,672 B2 5/2013 Matov et al.
8,562,338 B2 10/2013 Kitching et al.
8,591,225 B2 11/2013 Wu et al.
8,788,285 B2 7/2014 Kuo
8,843,381 B2 9/2014 Kuo et al.
8,874,452 B2 10/2014 Kuo
8,896,592 B2 11/2014 Boltunov et al.
8,930,219 B2 1/2015 Trosien et al.
9,037,439 B2 5/2015 Kuo et al.
9,060,829 B2 6/2015 Sterental et al.
9,125,709 B2 9/2015 Matty
9,211,166 B2 12/2015 Kuo et al.
9,220,580 B2 12/2015 Borovinskih et al.
9,364,296 B2 6/2016 Kuo
9,375,300 B2 6/2016 Matov et al.
9,414,897 B2 8/2016 Wu et al.
9,492,245 B2 11/2016 Sherwood et al.
9,642,678 B2 5/2017 Kuo
10,248,883 B2 4/2019 Borovinskih et al.
10,342,638 B2 7/2019 Kitching et al.
10,463,452 B2 11/2019 Matov et al.
10,595,966 B2 3/2020 Carrier, Jr. et al.
10,617,489 B2 4/2020 Grove et al.
10,722,328 B2 7/2020 Velazquez et al.
10,758,322 B2 9/2020 Pokotilov et al.
10,779,718 B2 9/2020 Meyer et al.
10,792,127 B2 10/2020 Kopelman et al.
10,828,130 B2 11/2020 Pokotilov et al.
10,835,349 B2 11/2020 Cramer et al.
10,973,611 B2 4/2021 Pokotilov et al.
10,996,813 B2 5/2021 Makarenkova et al.
10,997,727 B2 5/2021 Xue et al.
11,020,205 B2 6/2021 Li et al.
11,020,206 B2 6/2021 Shi et al.
11,026,766 B2 6/2021 Chekh et al.
11,033,359 B2 6/2021 Velazquez et al.
11,071,608 B2 7/2021 Derakhshan et al.
11,096,763 B2 8/2021 Akopov et al.
11,116,605 B2 9/2021 Nyukhtikov et al.
11,147,652 B2 10/2021 Mason et al.
11,151,753 B2 10/2021 Gao et al.
11,154,381 B2 10/2021 Roschin et al.
11,259,896 B2 3/2022 Matov et al.
11,357,598 B2 6/2022 Cramer
11,395,717 B2 7/2022 Yuryev et al.
11,432,908 B2 9/2022 Kopelman et al.
11,464,604 B2 10/2022 Makarenkova et al.
11,478,334 B2 10/2022 Matov et al.
11,484,389 B2 11/2022 Sterental et al.
11,521,732 B2 12/2022 Levin et al.
11,534,272 B2 12/2022 Li et al.
11,553,988 B2 1/2023 Mednikov et al.
12,465,464 B2* 11/2025 Wong .................. A61C 9/0086
2003/0008259 A1 1/2003 Kuo et al.
2003/0143509 A1 7/2003 Kopelman et al.
2003/0207227 A1 11/2003 Abolfathi
2004/0137400 A1 7/2004 Chishti et al.
2004/0152036 A1 8/2004 Abolfathi
2004/0197728 A1 10/2004 Abolfathi et al.
2004/0259049 A1 12/2004 Kopelman et al.
2005/0182654 A1 8/2005 Abolfathi et al.
2005/0244791 A1 11/2005 Davis et al.
2006/0127836 A1 6/2006 Wen
2006/0127852 A1 6/2006 Wen
2006/0127854 A1 6/2006 Wen
2006/0275731 A1 12/2006 Wen et al.
2006/0275736 A1 12/2006 Wen et al.
2008/0306724 A1 12/2008 Kitching et al.
2010/0009308 A1 1/2010 Wen et al.
2010/0068672 A1 3/2010 Arjomand et al.
2010/0068676 A1 3/2010 Mason et al.
2010/0092907 A1 4/2010 Knopp
2010/0167243 A1 7/2010 Spiridonov et al.
2013/0204599 A1 8/2013 Matov et al.
2016/0310235 A1 10/2016 Derakhshan et al.
2017/0273760 A1 9/2017 Morton et al.
2018/0280118 A1 10/2018 Cramer
2019/0029522 A1 1/2019 Sato et al.
2019/0029784 A1 1/2019 Moalem et al.
2019/0328487 A1 10/2019 Levin et al.
2019/0328488 A1 10/2019 Levin et al.
2020/0107915 A1 4/2020 Roschin et al.
2020/0155274 A1* 5/2020 Pimenov .................. G06T 7/60
2020/0160497 A1 5/2020 Shah et al.
2020/0297458 A1 9/2020 Roschin et al.
2020/0306011 A1 10/2020 Chekhonin et al.
2020/0306012 A1 10/2020 Roschin et al.

(56) References Cited

U.S. PATENT DOCUMENTS

| | | | | |
|---|---|---|---|---|
| 2020/0360109 | A1 | 11/2020 | Gao et al. | |
| 2021/0073998 | A1 | 3/2021 | Brown et al. | |
| 2021/0134436 | A1 | 5/2021 | Meyer et al. | |
| 2021/0174477 | A1 | 6/2021 | Shi et al. | |
| 2021/0196430 | A1* | 7/2021 | Wilson | A61C 7/002 |
| 2021/0338379 | A1 | 11/2021 | Salah et al. | |
| 2021/0361387 | A1 | 11/2021 | Salah et al. | |
| 2022/0023002 | A1 | 1/2022 | Cramer et al. | |
| 2022/0215928 | A1* | 7/2022 | Tabak | G16H 50/20 |
| 2023/0404709 | A1* | 12/2023 | Giegerich | A61B 1/247 |

OTHER PUBLICATIONS

Lo, Y.-C.; Chen, G.-A.; Liu, Y.-C.; Chen, Y.-H.; Hsu, J.-T.; Yu, J.-H. Prototype of Augmented Reality Technology for Orthodontic Bracket Positioning: An In Vivo Study. Appl. Sci. 2021, 11, 2315. https://doi.org/10.3390/app11052315 (Year: 2021).*

R. Winter, Recommended Photography Series. Spear Digest Dental Articles. https://www.speareducation.com/spear-review/2018/04/recommended-photography-series (Year: 2018).*

Litzenburger, F., Heck, K., Kaisarly, D. et al. Diagnostic validity of early proximal caries detection using near-infrared imaging technology on 3D range data of posterior teeth. Clin Oral Invest 26, 543-553. https://doi.org/10.1007/s00784-021-04032-1 (Year: 2021).*

Chen, H., Zhang, K., Lyu, P. et al. A deep learning approach to automatic teeth detection and numbering based on object detection in dental periapical films. Sci Rep 9, 3840 (2019). https://doi.org/10.1038/s41598-019-40414-y (Year: 2019).*

Tuzoff et al. Tooth detection and numbering in panoramic radiographs using convolutional neural networks. Dentomaxillofacial Radiology. 48, 4. https://doi.org/10.1259/dmfr.20180051 (Year: 2019).*

* cited by examiner

Intelligent Photo Guidance

Image Based Assessment

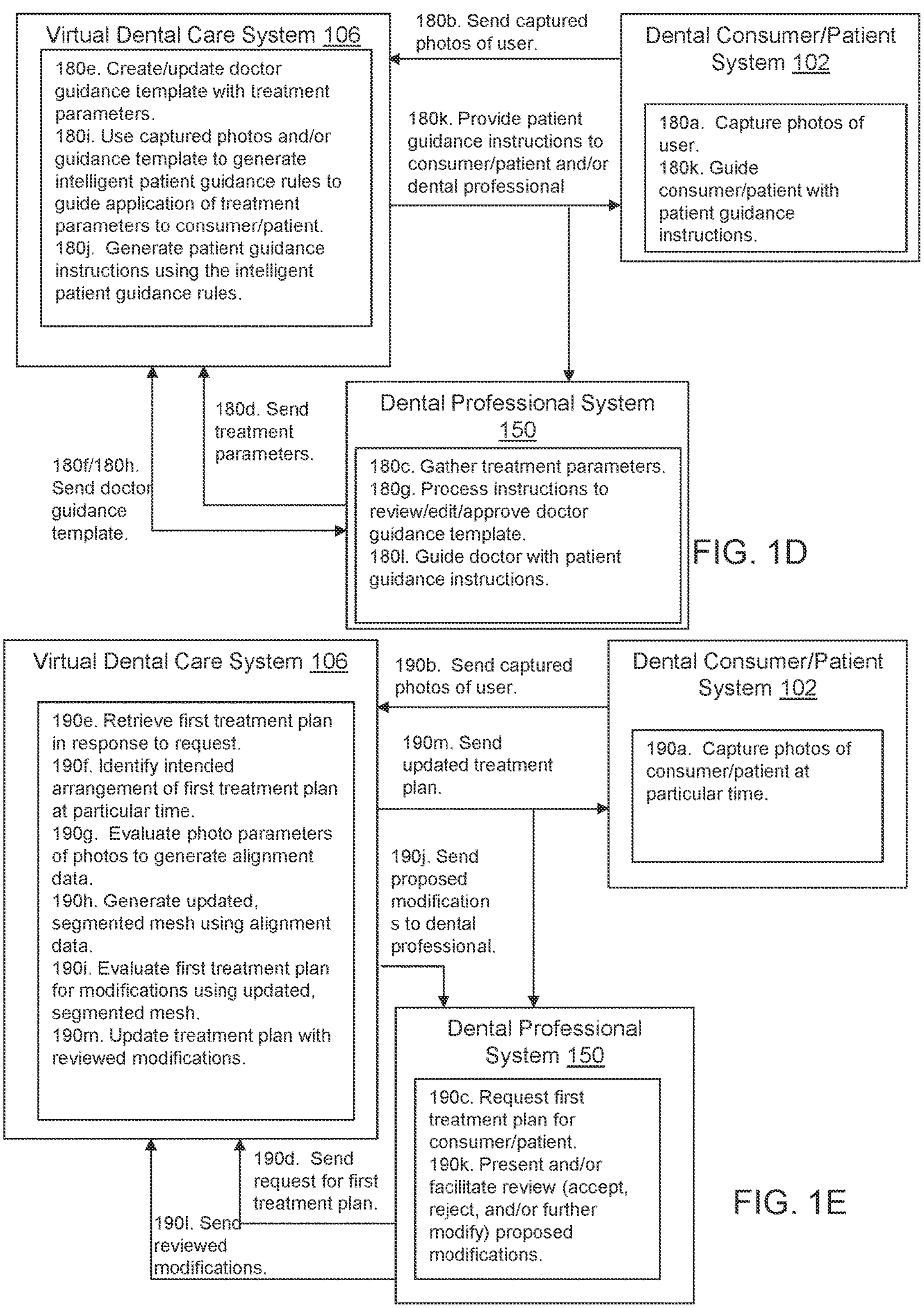
Virtual Dental Care System 106
180e. Create/update doctor guidance template with treatment parameters.
180i. Use captured photos and/or guidance template to generate intelligent patient guidance rules to guide application of treatment parameters to consumer/patient.
180j. Generate patient guidance instructions using the intelligent patient guidance rules.
180b. Send captured photos of user.
Dental Consumer/Patient System 102
180a. Capture photos of user.
180k. Guide consumer/patient with patient guidance instructions.
180k. Provide patient guidance instructions to consumer/patient and/or dental professional
180d. Send treatment parameters.
180f/180h. Send doctor guidance template.
Dental Professional System 150
180c. Gather treatment parameters.
180g. Process instructions to review/edit/approve doctor guidance template.
180l. Guide doctor with patient guidance instructions.
FIG. 1D
Virtual Dental Care System 106
190e. Retrieve first treatment plan in response to request.
190f. Identify intended arrangement of first treatment plan at particular time.
190g. Evaluate photo parameters of photos to generate alignment data.
190h. Generate updated, segmented mesh using alignment data.
190i. Evaluate first treatment plan for modifications using updated, segmented mesh.
190m. Update treatment plan with reviewed modifications.
190b. Send captured photos of user.
Dental Consumer/Patient System 102
190a. Capture photos of consumer/patient at particular time.
190m. Send updated treatment plan.
190j. Send proposed modification s to dental professional.
Dental Professional System 150
190c. Request first treatment plan for consumer/patient.
190k. Present and/or facilitate review (accept, reject, and/or further modify) proposed modifications.
190d. Send request for first treatment plan.
190l. Send reviewed modifications.
FIG. 1E

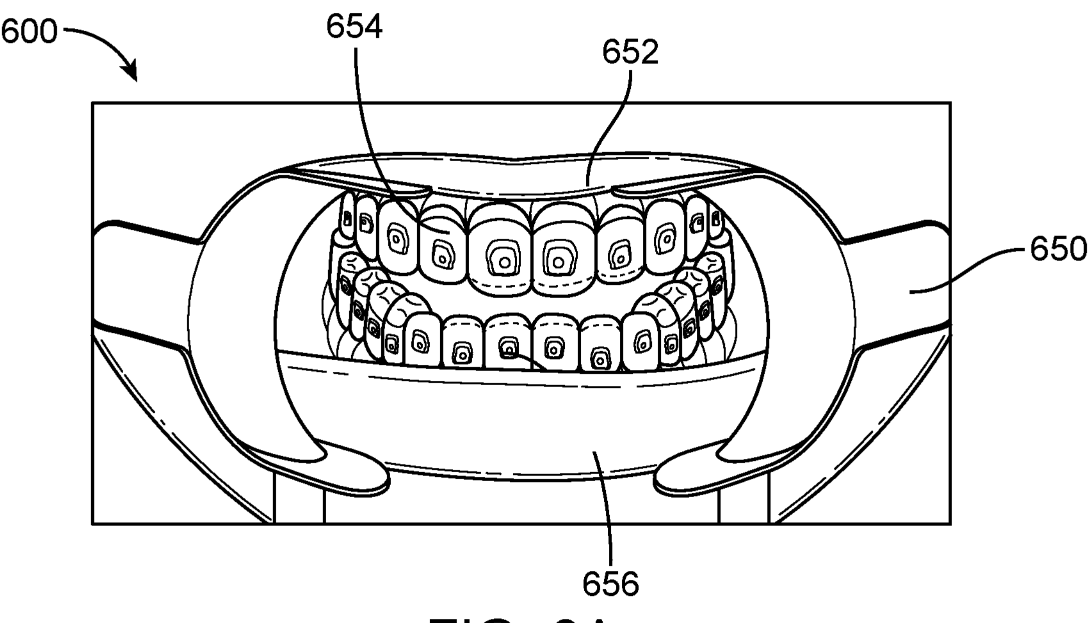
FIG. 6A
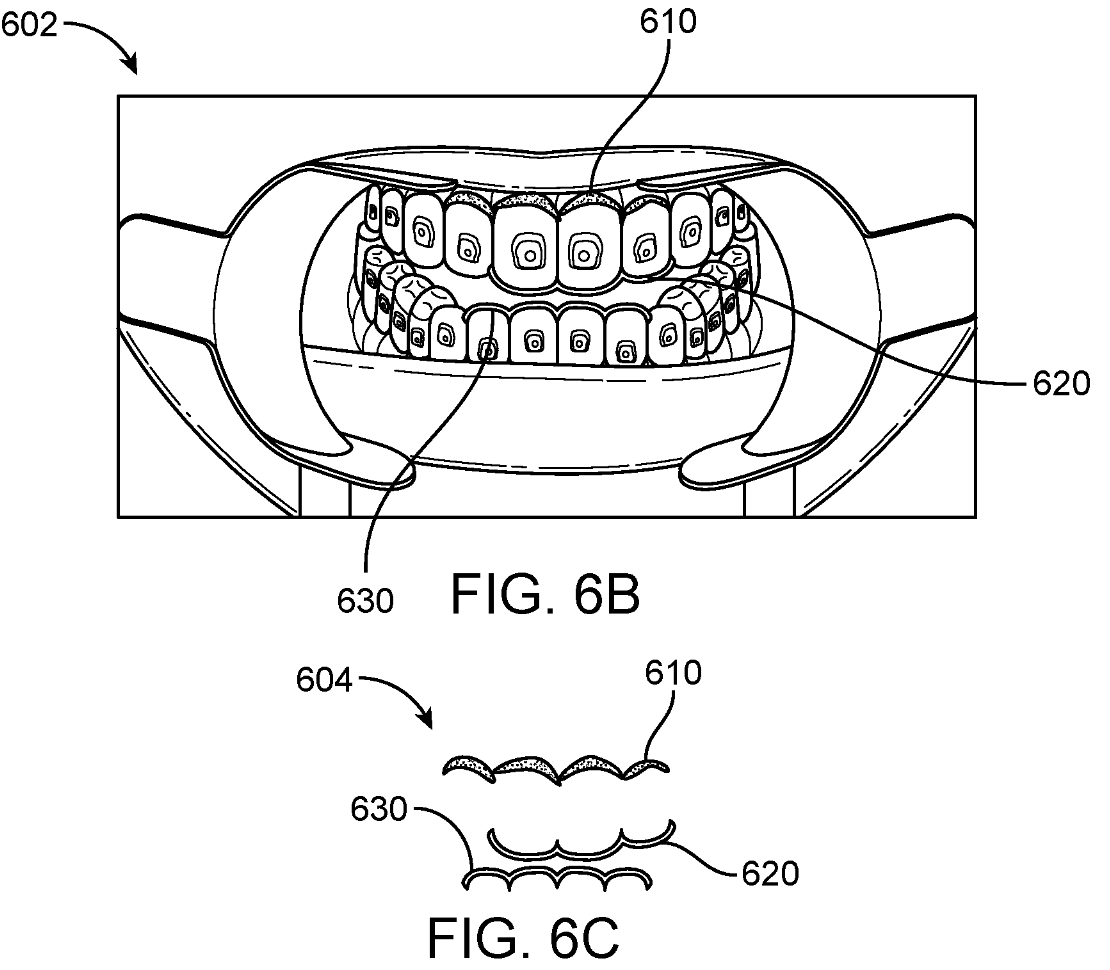
FIG. 6B
FIG. 6C

PHOTO-BASED DENTAL ATTACHMENT DETECTION

This application claims the benefit under 35 U.S.C. § 119(e) of U.S. Provisional Patent Application No. 63/301,412, filed Jan. 20, 2022, and titled "PHOTO-BASED DENTAL APPLIANCE AND ATTACHMENT TREATMENT," which is incorporated, in its entirety, by this reference.

The practice of medicine is evolving toward tele-medicine—the remote treatment of patients. Telemedicine allows doctors to assess the patient's needs, in some instances provide treatment suggestions for the patients without the hassle and risks involved in person treatments. However, current systems and methods related to dental care are less than desirable in many ways. For example, many dental care contexts require a patient to physically consult with a dentist for various purposes, such as initial assessments, obtaining diagnoses for various conditions, obtaining treatment plans and/or appliances prescribed by treatment plans, and tracking progress of a treatment. Existing dental care solutions reliant on live consultations and/or diagnoses are particularly problematic during times when dental offices are inaccessible due to emergencies, pandemics, physical inaccessibility, and/or impracticality.

SUMMARY

As will be described in greater detail below, the present disclosure describes various systems and methods for virtual dental care to remote patients, for example for assessing fit of a dental appliance and/or detecting attachments on patients' teeth.

In addition, the systems and methods described herein may improve the functioning of a computing device by reducing computing resources and overhead for acquiring and storing updated patient data, thereby improving processing efficiency of the computing device over conventional approaches. These systems and methods may also improve the field of orthodontic treatment by analyzing data to efficiently target treatment areas and providing patients with access to more practitioners than conventionally available.

INCORPORATION BY REFERENCE

All patents, applications, and publications referred to and identified herein are hereby incorporated by reference in their entirety, and shall be considered fully incorporated by reference even though referred to elsewhere in the application.

BRIEF DESCRIPTION OF THE DRAWINGS

A better understanding of the features, advantages and principles of the present disclosure will be obtained by reference to the following detailed description that sets forth illustrative embodiments, and the accompanying drawings of which:

FIG. 1D shows a block diagram of an example system for intelligent patient guidance, in accordance with some embodiments.

FIG. 1E shows a block diagram of an example system for photo-based refinement, in accordance with some embodiments.

FIGS. 6A-E show an example of gaps between an orthodontic appliance and a patient's dentition, in accordance with some embodiments.

DETAILED DESCRIPTION

The following detailed description and provides a better understanding of the features and advantages of the inventions described in the present disclosure in accordance with the embodiments disclosed herein. Although the detailed description includes many specific embodiments, these are provided by way of example only and should not be construed as limiting the scope of the inventions disclosed herein.

Virtual Care System

Figure 1A:
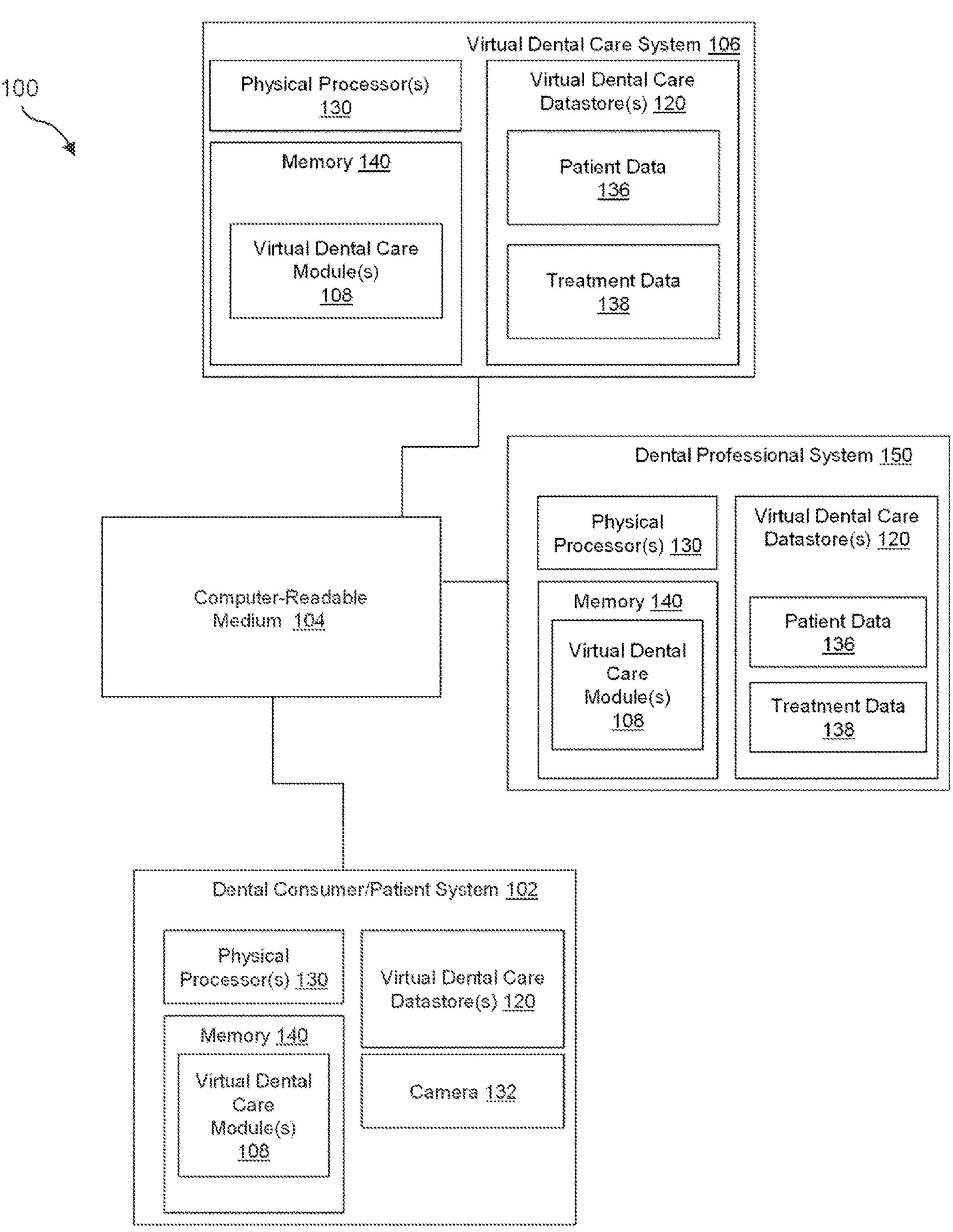
FIG. 1A shows a block diagram of an example system for virtual dental care, in accordance with some embodiments.

FIG. 1A shows a block diagram of an example system for virtual dental care, in accordance with some embodiments. As shown in FIG. 1A, system 100 may include a dental consumer/patient system 102, a dental professional system 150, a virtual dental care system 106, and a computer-readable medium 104. The dental consumer/patient system 102, dental professional system 150, and virtual dental care system 106 may communicate to one another over the computer-readable medium 104.

Dental consumer/patient system 102 generally represents any type or form of computing device capable of reading computer-executable instructions. Dental consumer/patient system 102 may be, for example, a desktop computer, a tablet computing device, a laptop, a smartphone, an augmented reality device, or other consumer device. Additional examples of dental consumer/patient system 102 include, without limitation, laptops, tablets, desktops, servers, cellular phones, Personal Digital Assistants (PDAs), multimedia players, embedded systems, wearable devices (e.g., smart watches, smart glasses, etc.), smart vehicles, smart packaging (e.g., active or intelligent packaging), gaming consoles, Internet-of-Things devices (e.g., smart appliances, etc.), variations or combinations of one or more of the same, and/or any other suitable computing device. The dental consumer/patient system 102 need not be a clinical scanner (e.g., an intraoral scanner), though it is contemplated that in some implementations, the functionalities described herein in relation to the dental consumer/patient system 102 may be incorporated into a clinical scanner. As an example of various implementations, the camera 132 of the dental consumer/patient system 102 may comprise an ordinary camera that captures 2D images of the patient's dentition and does not capture height-map and/or other data that is used to stitch a mesh of a 3D surface.

In some implementations, the dental consumer/patient system 102 is configured to interface with a dental consumer and/or dental patient. A "dental consumer," as used herein, may include a person seeking assessment, diagnosis, and/or treatment for a dental condition (general dental condition, orthodontic condition, endodontic condition, condition requiring restorative dentistry, etc.). A dental consumer may, but need not, have agreed to and/or started treatment for a dental condition. A "dental patient," as used herein, may include a person who has agreed to diagnosis and/or treatment for a dental condition. A dental consumer and/or a dental patient, may, for instance, be interested in and/or have started orthodontic treatment, such as treatment using one or more (e.g., a sequence of) aligners (e.g., polymeric appliances having a plurality of tooth-receiving cavities shaped to successively reposition a person's teeth from an initial arrangement toward a target arrangement). In various implementations, the dental consumer/patient system 102 provides a dental consumer/dental patient with software (e.g., one or more webpages, standalone applications, mobile applications, etc.) that allows the dental consumer/patient to capture images of their dentition, interact with dental professionals (e.g., users of the dental professional system 150), manage treatment plans (e.g., those from the virtual dental care system 106 and/or the dental professional system 150), and/or communicate with dental professionals (e.g., users of the dental professional system 150).

Dental professional system 150 generally represents any type or form of computing device capable of reading computer-executable instructions. Dental professional system 150 may be, for example, a desktop computer, a tablet computing device, a laptop, a smartphone, an augmented reality device, or other consumer device. Additional examples of dental professional system 150 include, without limitation, laptops, tablets, desktops, servers, cellular phones, Personal Digital Assistants (PDAs), multimedia players, embedded systems, wearable devices (e.g., smart watches, smart glasses, etc.), smart vehicles, smart packaging (e.g., active or intelligent packaging), gaming consoles, Internet-of-Things devices (e.g., smart appliances, etc.), variations or combinations of one or more of the same, and/or any other suitable computing device.

In various implementations, the dental professional system 150 is configured to interface with a dental professional. A "dental professional" (used interchangeably with dentist, orthodontist, and doctor herein) as used herein, may include any person with specialized training in the field of dentistry, and may include, without limitation, general practice dentists, orthodontists, dental technicians, dental hygienists, etc. A dental professional may include a person who can assess, diagnose, and/or treat a dental condition. "Assessment" of a dental condition, as used herein, may include an estimation of the existence of a dental condition. An assessment of a dental condition need not be a clinical diagnosis of the dental condition. In some embodiments, an "assessment" of a dental condition may include an "image based assessment," that is an assessment of a dental condition based in part or on whole on photos and/or images (e.g., images that are not used to stitch a mesh or form the basis of a clinical scan) taken of the dental condition. A "diagnosis" of a dental condition, as used herein, may include a clinical identification of the nature of an illness or other problem by examination of the symptoms. "Treatment" of a dental condition, as used herein, may include prescription and/or administration of care to address the dental conditions. Examples of treatments to dental conditions include prescription and/or administration of brackets/wires, clear aligners, and/or other appliances to address orthodontic conditions, prescription and/or administration of restorative elements to address bring dentition to functional and/or aesthetic requirements, etc. The dental professional system 150 may provide to a user software (e.g., one or more webpages, standalone applications (e.g., dedicated treatment planning and/or treatment visualization applications), mobile applications, etc.) that allows the user to interact with users (e.g., users of the dental consumer/patient system 102, other dental professionals, etc.), create/modify/manage treatment plans (e.g., those from the virtual dental care system 106 and/or those generated at the dental professional system 150), etc.

Virtual dental care system 106 generally represents any type or form of computing device that is capable of storing and analyzing data. Virtual dental care system 106 may include a backend database server for storing patient data and treatment data. Additional examples of virtual dental care system 106 include, without limitation, security servers, application servers, web servers, storage servers, and/or database servers configured to run certain software applications and/or provide various security, web, storage, and/or database services. Although illustrated as a single entity in FIG. 1A, virtual dental care system 106 may include and/or represent a plurality of servers that work and/or operate in conjunction with one another.

As illustrated in FIG. 1A, dental consumer/patient system 102, virtual dental care system 106, and/or dental professional system 150 may include one or more memory devices, such as memory 140. Memory 140 generally represents any type or form of volatile or non-volatile storage device or medium capable of storing data and/or computer-readable instructions. In one example, memory 140 may store, load, execute in conjunction with physical processor(s) 130, and/or maintain one or more of virtual dental care modules 108. Examples of memory 140 include, without limitation, Random Access Memory (RAM), Read Only Memory (ROM), flash memory, Hard Disk Drives (HDDs), Solid-State Drives (SSDs), optical disk drives, caches, variations or combinations of one or more of the same, and/or any other suitable storage memory.

As illustrated in FIG. 1A, dental consumer/patient system 102, dental professional system 150, and/or server 106 may also include one or more physical processors, such as physical processor(s) 130. Physical processor(s) 130 generally represents any type or form of hardware-implemented processing unit capable of interpreting and/or executing computer-readable instructions. In one example, physical processor(s) 130 may access and/or modify one or more of virtual dental care modules 108 stored in memory 140. Additionally or alternatively, physical processor 130 may execute one or more of virtual dental care modules 108 to facilitate virtual care. Examples of physical processor(s) 130 include, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, and/or any other suitable physical processor.

In some embodiments, dental consumer/patient system 102 may include a camera 132. Camera 132 may comprise a camera, scanner, or other optical sensor. Camera 132 may include one or more lenses or may, one or more camera devices, and/or one or more other optical sensors. In some examples, camera 132 may include other sensors and/or devices which may aid in capturing optical data, such as one or more lights, depth sensors, etc. In various implementations, the camera 132 is not a clinical scanner.

Computer-readable medium 104 generally represents any transitory or non-transitory computer-readable medium or architecture capable of facilitating communication or data transfer. In one example, computer-readable medium 104 may facilitate communication between dental consumer/patient system 102, dental professional system 150, and/or virtual dental care system 106. In some implementations, computer-readable medium 104 comprises a computer network that facilitates communication or data transfer using wireless and/or wired connections. Examples of computer-readable medium 104 include, without limitation, an intranet, a Wide Area Network (WAN), a Local Area Network (LAN), a Personal Area Network (PAN), the Internet, Power Line Communications (PLC), a cellular network (e.g., a Global System for Mobile Communications (GSM) network), portions of one or more of the same, variations or combinations of one or more of the same, and/or any other suitable network. Computer-readable medium 104 may also comprise a connection between elements inside a single device (e.g., a bus, any communications infrastructure (e.g., communication infrastructure 1012 shown in FIG. 10, etc.).

Virtual dental care datastore(s) 120 include one or more datastore configured to store any type or form of data that may be used for virtual dental care. In some embodiments, the virtual dental care datastore(s) 120 include, without limitation, patient data 136 and treatment data 138. Patient data 136 may include data collected from patients, such as patient dentition information, patient historical data, patient scans, patient information, etc. Treatment data 138 may include data used for treating patients, such as treatment plans, state of treatment, success of treatment, changes to treatment, notes regarding treatment, etc.

Example system 100 in FIG. 1A may be implemented in a variety of ways. For example, all or a portion of example system 100 may represent portions of example system 200 in FIG. 2, system 1000 in FIG. 10, and/or system 1100 in FIG. 11.

As will be described in greater detail below, one or more of virtual dental care modules 108 and/or the virtual dental care datastore(s) 120 in FIG. 1A may, (when executed by at least one processor of dental consumer/patient system 102, virtual dental care system 106, and/or dental professional system 150) enable dental consumer/patient system 102, virtual dental care system 106, and/or dental professional system 150 to facilitate providing virtual dental care between a doctor and a patient. "Virtual dental care," as used herein, may include computer-program instructions and/or software operative to provide remote dental services by a health professional (dentist, orthodontist, dental technician, etc.) to a patient, a potential consumer of dental services, and/or other individual. Virtual dental care may comprise computer-program instructions and/or software operative to provide dental services without a physical meeting and/or with only a limited physical meeting. As an example, virtual dental care may include software operative to providing dental care from the dental professional system 150 and/or the virtual dental care system 106 to the computing device 102 over the network 104 through e.g., written instructions, interactive applications that allow the health professional and patient/consumer to interact with one another, telephone, chat etc. "Remote dental care," as used herein, may comprise computer-program instructions and/or software operative to provide a remote service in which a health professional provides a patient with dental health care solutions and/or services. In some embodiments, the virtual dental care facilitated by the elements of the system 100 may include non-clinical dental services, such as dental administration services, dental training services, dental education services, etc.

Figure 1B:
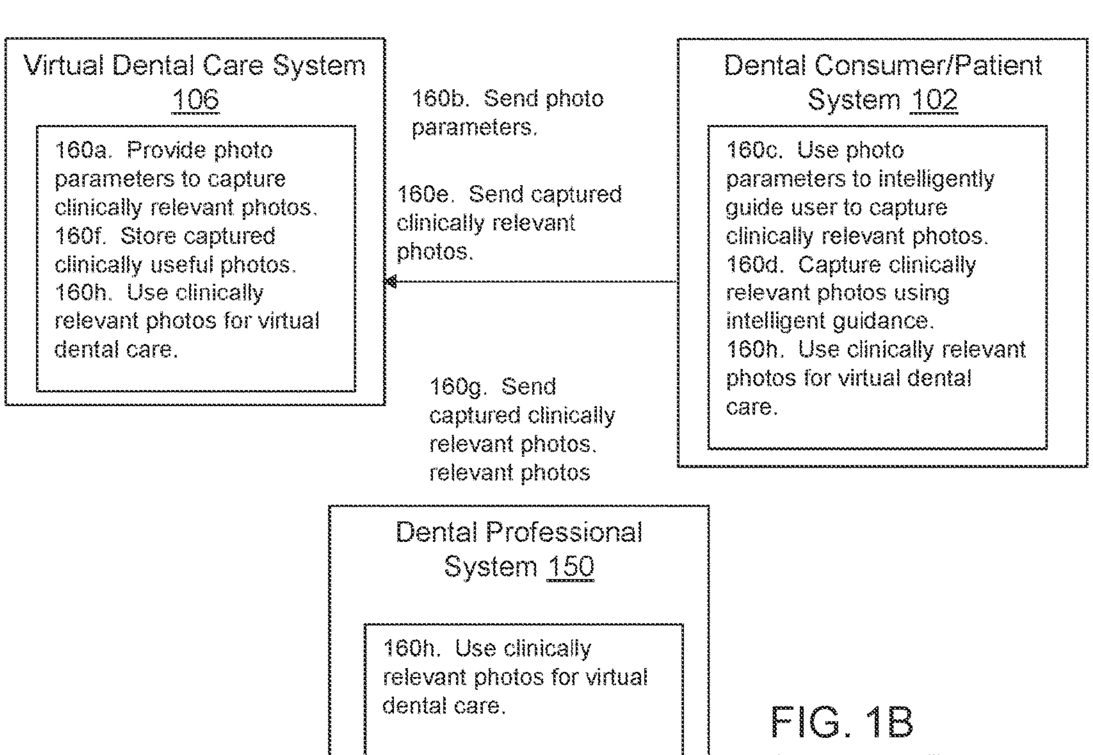
FIG. 1B shows a block diagram of an example system for intelligent photo guidance, in accordance with some embodiments.

In some embodiments, the elements of the system 100 (e.g., the virtual dental care modules 108 and/or the virtual dental care datastore(s) 120) may be operative to provide intelligent photo guidance to a patient to take images relevant to virtual dental care using the camera 132 on the computing device 102. An example of how the elements of the system 100 may operate to provide intelligent photo guidance is shown in FIG. 1B.

At an operation 160*a*, the virtual dental care system 106 may provide one or more photo parameters to capture clinically relevant photos of a user. "Clinically relevant" and/or "clinically acceptable" photos, as used herein, may include images that represent the state of dental conditions in a consumer/patient's dentition. Clinically relevant photos may include photos that are sufficient to provide current position(s) and/or orientation(s) of the teeth in a consumer/patient's mouth. Examples of clinically relevant photos include photos that show all the teeth in a consumer/patient's arch; photos that show the shape of a consumer/patient's arch; photos that show locations of teeth that are missing, supernumerary, ectopic, etc.; photos that show malocclusions in a consumer/patient's arch (e.g., from front, left buccal, right buccal, and/or other various perspectives); photos that show whether or not cheek retractors or a scanning box device with retractors or cheek retraction structures and being coupled to a mobile phone were used during the image capture process; photos that show posterior teeth, etc. "Photo parameters," as used this context, may include parameters to define clinically acceptable criteria (e.g., clinically acceptable position(s) and/or clinically acceptable orientation(s) of teeth) in one or more photos. Photo parameters can include a distance parameters, e.g., one that parametrizes a distance that a camera is relative to a consumer/patient's dentition; orientation parameters (e.g., those that parametrize orientations of photos taken of teeth); openness parameters of a photo of a consumer/patient's bite (e.g., whether a bite is open, closed, and/or a degree of openness of a bite); a dental appliance wear parameter of a photo of a consumer/patient's bite (e.g., whether a photo shows dental appliances, such as cheek retractors, scanning box device, aligners, etc. in a consumer/patient's mouth); camera parameters (brightness parameters of photos; contrast parameters of photos; exposure parameters of photos; etc.); tooth identifier parameters, e.g., those that parametrize the specific teeth in a photo, those taken from a treatment plan; etc. At an operation 160*b*, the virtual care dental system 106 may send the one or more photo parameters to the dental consumer/patient system 102. This operation can occur as a file and/or data transfer over the computer-readable medium 104.

At an operation 160$c$, the dental consumer/patient system 102 may use the one or more photo parameters to intelligently guide the consumer/patient to capture clinically relevant photos of their dentition. The dental consumer/patient system 102 may gather image-capture rules that guide capturing the clinically relevant photos based on the photo parameters. The dental consumer/patient system 102 may provide a consumer/patient with software (e.g., one or more webpages, standalone applications, mobile applications, etc.) that uses the one or more photo parameters to help the consumer/patient capture clinically relevant photos of their teeth. As an example, distance parameters may be used to guide a consumer/patient to position and/or orient the dental consumer/patient system 102 a specific distance away from their teeth to capture a photo with appropriate details of their teeth. The distance parameters may guide whether the position of a camera is too close or too far or just right. Orientation parameters may be used to guide a photo to clinically relevant orientations. As an example, orientation parameters may be used to guide a consumer/patient to take photos of anterior views, left buccal views, right buccal views, etc. As additional examples, openness parameters may be used to guide a consumer/patient to take photos of various bite states, e.g., an open bite, closed bite, and/or a bite that is partially open in order to be clinically relevant; dental appliance wear parameters may be used to detect cheek retractors, canning boxes, and/or guide a consumer/patient to position cheek retractors appropriately and/or locate/orient photos to be clinically relevant; dental appliance wear parameters may be used to detect various dental appliances (aligners, retainers, etc.) and guide a consumer to remove, move, etc. the dental appliances for photos that are clinically relevant; etc. Additionally, tooth identifier parameters (e.g., those gathered from a treatment plan) can be used to guide a consumer/patient to take photos of a sufficient number of teeth so that the photos are clinically relevant. Camera parameters, e.g., contrast, brightness, exposure, etc. parameters may be used to guide consumers/patients to take photos that have properties such that the photos are clinically relevant. In some implementations, the dental consumer/patient system 102 uses camera parameters to modify one or more photo settings (add/disable flash, adjust zoom, adjust brightness, adjust contrast, adjust shadows, adjust silhouettes, etc. so that clinically relevant photos are captured under various conditions. As noted herein, the operation 160$c$ may be performed by automated agents and without human intervention.

At an operation 160$d$, the dental consumer/patient system 102 may operate to capture clinically relevant photos using the intelligent guidance. In some implementations, a consumer/patient may follow instructions to capture photos of their dentition using the intelligent guidance provided on the dental consumer/patient system 102. In various implementations, at least a part of operation 160$d$ is performed by automated agents that configure a camera to take photos without human intervention. At an operation 160$e$, the dental consumer/patient system 102 may send captured clinically relevant images to the virtual dental care system 106. This operation may occur as a file and/or data transfer over the computer-readable medium 104.

At an operation 160$f$, the virtual dental care system 106 may store the captured clinically relevant photos. In various implementations, the virtual dental care system 106 may store the captured clinically relevant photos in a treatment database associated with a consumer/patient, a clinical data file associated with a consumer/patient, and/or in any relevant datastore. At an operation 160$g$, the virtual dental care system 106 may send captured clinically relevant photos to the dental consumer/patient system 102 and/or the dental professional system 150. This operation may occur over a file and/or data transfer over the computer-readable medium 104.

At an operation 160$h$, the dental consumer/patient system 102, the virtual dental care system 106 and/or the dental professional system 150 may use clinically relevant photos for virtual dental care. As an example, the dental professional system 150 may display to the consumer/patient instructions in the form of an overlay over an image of the consumer/patient's teeth. As an other example, the dental professional system 150 may display to the consumer/patient verbal and/or interactive instructions on how to modify and/or improve capture of a clinically relevant photo. In some implementations, the dental consumer/patient system 102, the virtual dental care system 106 and/or the dental professional system 150 may, e.g., use clinically relevant photos for image-based assessments, intelligent patient guidance, and/or photo-based refinements.

Figure 1C:
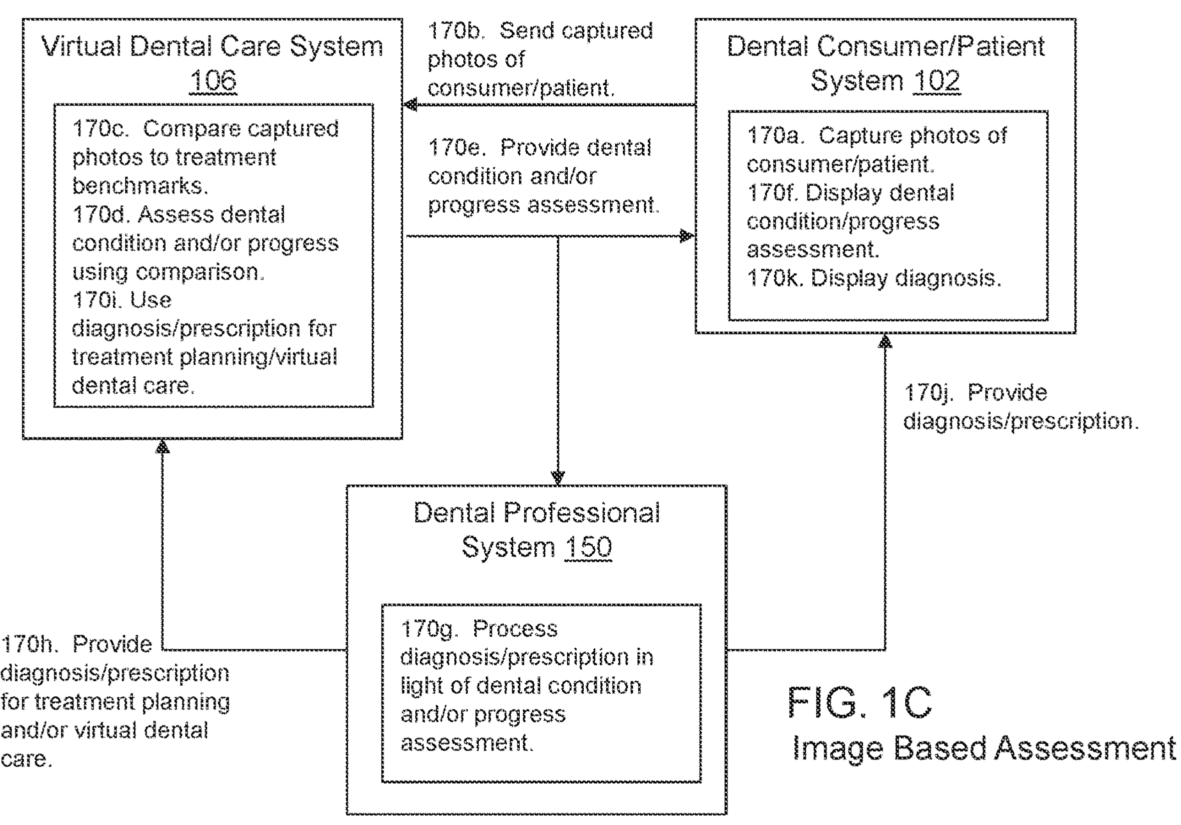
FIG. 1C shows a block diagram of an example system for image-based assessment, in accordance with some embodiments.

In some embodiments, the elements of the system 100 (e.g., the virtual dental care modules 108 and/or the virtual dental care datastore(s) 120) may be operative to provide one or more image-based assessment tools to the users of the dental professional system 150. "Image-based assessment tools," as used herein, may include digital tools that operate to provide image-based assessments of a dental condition. In some embodiments, image-based assessments may comprise visualizations that allow a user of the dental professional system 150 to make a decision about a clinical condition. For instance, the elements of the system 100 may provide visualizations that assist a user of the dental professional system 150 with one or more diagnoses of a dental condition. As noted herein, visualizations may include, e.g., visualizations of assessments of a current stage of a treatment plan; visualizations of assessments may, but need not, be based on images and knowledge of a treatment plan that is underway. As another example, the elements of the system 100 may provide visualizations to a user of the dental professional system 150 that provide a view of a patient's assessment over time. An example of how the elements of the system 100 may operate to provide image-based assessment tools is shown in FIG. 1C.

At an operation 170$a$, the dental consumer/patient system 102 may capture one or more images of a consumer/patient. The one or more images may comprise photos taken by the camera of the dental consumer/patient system 102. The one or more photos may be captured by intelligent photo guidance techniques described further herein. The one or more images may include various perspectives and/or views of the dentition of the consumer/patient. The one or more photos captured at operation 170$a$ need not include scan data, height map information, and/or data a clinical scanner uses to stitch together a mesh representation of consumer/patient's dentition. The dental consumer/patient system 102 may store images captured locally, in a networked folder, etc. At an operation 170$b$, the dental consumer/patient system 102 may send captured photos of the consumer/patient to the virtual dental care system 106. This operation may include a file and/or other data transfer over the computer-readable medium 104.

At an operation 170$c$, the virtual dental care system 106 may compare the captured photos to one or more treatment benchmarks. "Treatment benchmarks," as used herein, may include one or more standards or reference points of at least part of a treatment plan. Treatment benchmarks may include intended positions of teeth, jaws, palatal regions, etc. of dentition at a specific stage of a treatment plan. In some implementations, treatment benchmarks are represented as intended positions of a specific stage of a treatment plan on a 3D model of a patient's dentition. In various implementations, treatment benchmarks correspond to representations of a patient's dentition from which to assess a dental condition. As examples, treatment benchmarks may represent a variety of malocclusions for which the consumer/patient is to be assessed. At an operation 170*d*, the virtual care dental system 106 may assess a dental condition and/or progress of a treatment plan using the comparison of the captured photos and the treatment benchmarks. As noted herein, the assessment need not comprise a diagnosis of the dental condition and/or the progress through the treatment plan.

At an operation 170*e*, the virtual dental care system 106 may provide the dental consumer/patient system 102 and/or the dental professional system 150 the assessed dental condition and/or the progress assessment. This operation may occur as a file and/or data transfer over the computer-readable medium 104. The dental consumer/patient system 102 and/or the dental professional system 150 may perform additional operations with the assessed dental condition and/or the progress assessment. As one example, the dental consumer/patient system 102 may, at an operation 170*f*, display the dental condition and/or the progress assessment. For instance, the dental consumer/patient system 102 may display, e.g., in an application and/or in webpages, user interface elements (annotated 3D models, annotated images, informative and/or interactive user interface elements, etc.) that show an assessment to a consumer/patient.

As another example, the dental professional system 150 may, in an operation 170*g*, process a diagnosis and/or prescription for a consumer/patient using the dental condition and/or progress assessment. In the operation 170*g*, the diagnosis may also be based on one or more clinical images (intraoral scans, x-rays, CBCT scans, etc.) of the consumer/patient's dentition. In some implementations, a doctor may use software on the dental professional system 150 to perform a diagnosis of a dental condition and/or of progress of a treatment plan. As an example, a doctor may use treatment planning software on the dental professional system 150 to diagnose malocclusions and/or other dental conditions reflected in the photos from the consumer/patient. Instructions corresponding to the diagnosis may be processed by the dental professional system 150. In various implementations, a dental professional may provide a prescription to treat one or more dental conditions. As an example, a dental professional may prescribe through the dental professional system 150 one or more dental appliances (clear aligners, orthodontic appliances, restorative appliances, etc.) to treat dental conditions that are associated with the dental condition and/or progress assessment. For an initial assessment, the prescription may comprise an initial prescription for dental appliances. For a progress assessment, the prescription may comprise corrective dental appliances that are configured to correct deviation(s) from a treatment plan.

At an operation 170*h*, the dental professional system 150 may provide the diagnosis and/or prescription for treatment planning and/or virtual dental care to the virtual dental care system 106. At an operation 170*i*, the virtual care dental system 106 may use the diagnosis/prescription for treatment planning and/or virtual dental care. At an operation 170*j*, the dental professional system 150 may provide the diagnosis and/or prescription to the dental consumer/patient system 102. At an operation 170*k*, the dental consumer/patient system 102 may display the diagnosis to the consumer/patient.

In some embodiments, the elements of the system 100 (e.g., the virtual dental care modules 108 and/or the virtual dental care datastore(s) 120) may be operative to provide intelligent patient guidance to consumers/patients that use the dental consumer/patient system 102. "Intelligent patient guidance," as used herein, may include instructions to guide a consumer/patient to take one or more actions. In some implementations, the elements of the system 100 generate intelligent patient guidance using photos of a consumer/patient, treatment parameters supplied by a doctor, and/or other information.

In some implementations, intelligent patient guidance is supplied by automated agents without intervention (or with minimal intervention, e.g., a doctor providing treatment parameters and/or interacting with a guidance template). Intelligent patient guidance may include: e.g., instructions to change (and/or when to change) a specific dental appliance (e.g., an aligner, a retainer, etc.); instructions to continue use (and/or when to continue use) of a dental appliance in relation to a subsequent dental appliance, instructions to use (and/or a location of use) of a supplemental dental appliance (e.g., chewie, mint, etc.); instructions to direct attention to a region of a consumer/patient's dentition (anterior portions, posterior portions, portions that are likely to move during a specific stage, portions that anchor various tooth movements, etc.); instructions to notify a doctor at a specific time or in response to a specific event (e.g., teeth moving at a specific time, teeth moving in accordance with a specific movement pattern, etc.); instructions to capture one or more images of a consumer/patient's dentition for the purpose of progress tracking at a specified time/treatment stage; instructions to the consumer/patient to visit a doctor, set an appointment, or take other action in relation to a doctor; etc. As noted herein, intelligent patient guidance can include any combination and/or variations of the foregoing examples.

Intelligent patient guidance may accommodate deconfliction, e.g., may be determined based on prioritizing some forms of action and/or removing some conflicting forms of action from guidance. Guidance Rules may provide a set of conflicting or prioritized guidance to the patient. E.g., use a chewie (due to one rule) and set an appointment (due to another) and have the system alert the doctor (due to a third rule); in a case such as this, only a alert to a doctor rule might be activated because the doctor may override the other rules. Another example might be the rules indicating the use of a chewie on the first premolar and another rule indicating a chewie on the second premolar on the same side—clearly only one chewie is needed. Deconfliction may ensure that patient is provided with only relevant guidance.

Intelligent patient guidance supplied by the elements of the system 100 may be based on a dental condition and/or progress assessment (e.g., one reflected by images captured by a consumer/patient), treatment parameters, etc. "Treatment parameters," as used herein, may include a set of parameters that are used to specify attributes of a treatment plan to apply to a consumer/patient. Treatment parameters may include doctor-preference parameters, e.g., treatment parameters specifying treatment protocols that a doctor (and/or other doctors, e.g., those whose treatment protocols are used by a specific doctor) would prescribe for various patients and/or clinical conditions. Treatment parameters may include per-patient parameters, e.g., parameters used to specify treatment protocols for a specific consumer/patient. Per-patient parameters may be based on attributes of a consumer/patient (past treatments, anatomical information (attributes of specific dentitions, jaws, etc.), etc. Per-patient parameters need not be based on attributes of a specific consumer/patient, and, e.g., may include demographic information (information related to the consumer/patient's race, gender, age, etc.), information about historically treated cases (e.g., those with similar forms of dental conditions to the consumer/patient) information about idealized dental arches (e.g., those related to dental arches with idealized/near-idealized occlusions as defined by treatment professionals), and/or other information.

In some implementations, the elements of the system 100 may utilize a doctor guidance template, which, as used herein, may include a formatted data structure that specifies a set of rules that a doctor can use for tracking a treatment plan. Examples of rules could be as specific as central incisors deviations from the treatment plan of 0.75 millimeters (mm) should result in a new appointment; central incisor deviations of 0.5-0.75 mm should be watched; central incisor deviations that increase over a period of two (2) months should result in a new appointment; central incisor deviations of 0.25 to 0.5 mm should wear the current set of aligners for an additional week; and central incisor deviations less than 0.25 mm can be considered "on-track". Other rules may specify that teeth marked "Do No Move" should not deviate from their treatment position and any deviation greater than 0.25 mm should result in an appointment. Rules in a doctor guidance template may allow conditionals based on a treatment plan and/or other factors. In some implementations, rules in a doctor guidance template may be written with a temporal frame of reference and/or based on patient historical data (e.g., historical information about patient guidance provided to a consumer/patient in the past and/or historical measurement information). An example of how the elements of the system 100 may operate to provide intelligent patient guidance is shown in FIG. 1D.

At an operation 180*a*, the dental consumer/patient system 102 may capture one or more images of a consumer/patient. The one or more images may comprise photos taken by the camera of the dental consumer/patient system 102. The one or more photos may be captured by intelligent photo guidance techniques described further herein. The one or more images may include various perspectives and/or views of the dentition of the consumer/patient. The one or more photos captured at operation 180*a* need not include scan data, height map information, and/or data a clinical scanner uses to stitch together a mesh representation of consumer/patient's dentition. The one or more photos may reflect a state of a treatment plan that is intended for and/or is underway on the consumer/patient. As an example, the one or more photos may capture an initial assessment of the consumer/patient's dentition and/or reflect the patient's progress at a specified stage of a treatment plan. The dental consumer/patient system 102 may store images captured locally, in a networked folder, etc. At an operation 180*b*, the dental consumer/patient system 102 may send captured photos of the consumer/patient to the virtual dental care system 106. This operation may include a file and/or other data transfer over the computer-readable medium 104.

At an operation 180*c*, the dental professional system 150 may gather treatment parameters for the consumer/patient. As noted herein, the treatment parameters may include doctor-preference parameters, per-patient parameters, etc. At an operation 180*d*, the dental professional system 150 may send the treatment parameters to the virtual dental care system 106. This operation may include a file and/or transfer over the computer-readable medium 104. As noted herein, the treatment parameters may comprise doctor-preference parameters and/or per-patient parameters.

At an operation 180*e*, the virtual dental care system 106 may create and/or update a doctor guidance template with treatment parameters. As noted herein, the doctor guidance template may supply a template with one or more rules that a doctor can use to track implementation of a treatment plan to a consumer/patient. The doctor guidance template may accommodate one or more rules to perform guidance deconfliction and/or prioritize various forms of action given doctor preferences, patient attributes, etc. The virtual dental care system 106 may store a doctor guidance template in any relevant format, including but not limited to any transitory and/or non-transitory medium. The virtual dental care system 106 may, in an operation 180*f*, send a doctor guidance template to the dental professional system 150.

At an operation 180*g*, the dental professional system 150 may process instructions to review, edit, and/or approve a doctor guidance template. In some implementations, the dental professional system 150 may provide a doctor with a user interface and/or other software that allows the doctor to review doctor guidance templates, make any changes to a doctor guidance template, and/or approve/finalize a doctor guidance template so that it can be applied to a specific patient, such as the consumer/patient using the dental consumer/patient system 102. As an example, in some implementations, a doctor may provide instructions to override a specific part of a doctor guidance template based on one or more factors, such as factors related to specific attributes of a specific consumer/patient. The dental professional system 150 may, in an operation 180*h*, send a reviewed/edited/approved doctor guidance template to the virtual dental care system 106. This operation may occur as a file and/or data transfer over the computer-readable medium 104.

At an operation 180*i*, the virtual dental care system 106 may use the captured photos and optionally the guidance template to generate intelligent patient guidance rules (e.g., rules that guide application of the treatment parameters to the consumer/patient). In some implementations, the virtual care dental system 106 may use the captured photos that were captured at the dental consumer/patient system 102 and a doctor guidance template reviewed, edited, and/or approved by the dental professional system 150 to generate intelligent patient guidance rules for the consumer/patient. At an operation 180*j*, the virtual care dental system 106 can generate patient guidance instructions using the intelligent patient guidance rules. Patient guidance instructions may take the form of instructions to the consumer/patient to take specific actions (add/change a dental appliance, wear a dental appliance longer or shorter than initially prescribed), may take the form of instructions to modify appointments and/or tasks, and/or may take the form of instructions to interact with the doctor in new and/or modified ways (e.g., draw attention to an area of dentition that is of increased interest).

At an operation 180*k*, the virtual dental care system 106 may provide patient guidance instructions to the dental consumer/patient system 102 and/or the dental professional system 150. This operation may occur as a file and/or data transfer over the computer-readable medium 104.

At an operation 180*k*, the dental consumer/patient system 102 may guide a consumer/patient using patient guidance instructions. In various implementations, the dental/consumer system 102 may present a consumer/patient with automated and/or interactive software elements that instruct the consumer/patient to take specified actions in relation to their treatment plans. As noted herein, example actions include instructions to change a dental appliance, instructions to keep a dental appliance beyond an initially prescribed time, use a supplemental dental appliance at a specific time/location, set an appointment for a specific condition and/or at a specific time/place, etc. At an operation **180*l*, the dental professional system 150 may guide the doctor with patient guidance instructions. In various implementations, the dental professional system 150** may present a doctor with automated and/or interactive software elements that, e.g., set appointments for a patient, notify a doctor about one or more conditions and/or regions of a consumer/patient's dentition to focus on, etc.

In some embodiments, the elements of the system 100 (e.g., the virtual dental care modules 108 and/or the virtual dental care datastore(s) 120) may be operative to provide photo-based refinements to users of the dental professional system 150. "Photo-based refinements," as used herein, may include tools that allow a doctor performing virtual dental care to prescribe orders for consumers/patients whose treatments deviate from an intended course of treatment. The tools may use photos and may avoid requirements to rescan (e.g., perform a second and/or subsequent clinical scan after an initial clinical scan) the consumer/patient and/or provide a live evaluation of the consumer/patient, e.g., at the doctor's office. In some implementations, photo-based refinements may provide tools for a doctor to create a secondary (e.g., a refined) treatment plan remotely without ever physically seeing and/or evaluating a consumer/patient. Photo-based refinements may optimize one or more camera parameters to align a consumer/patient's treatment plan to photos captured by/for the consumer/patient. Photo-based refinements may also optimize one or more pose parameters (e.g., location parameters, orientation parameters, etc.) of a consumer/patient's teeth to ensure the teeth are in appropriate spaces. As noted herein, photo-based refinements may be displayed to doctors as user interface elements (e.g., overlays) representing a consumer/patient's dentition in relation to a treatment plan. Photo-based refinements can be used to plan one or more refinement treatment plans using 3D tooth shapes from a primary treatment plan and/or locations found using the techniques described herein; as noted herein, this information may be used to plan one or more new/refined treatment plans. An example of how the elements of the system 100 may operate to provide photo-based refinements is shown in FIG. 1E.

At an operation **190*a*, the dental consumer/patient system 102 may capture one or more images of a consumer/patient at a particular time, e.g., at one or more time during the course of virtual dental care. The one or more images may comprise photos taken by the camera of the dental consumer/patient system 102. The one or more photos may be captured by intelligent photo guidance techniques described further herein. The one or more images may include various perspectives and/or views of the dentition of the consumer/patient. As an example, the one or more images may include a plurality of images that represent more than one perspective of the consumer/patient's dentition. For instance, the images may be taken from anterior, left buccal, right buccal, and/or other perspectives. As noted herein, the one or more images may be captured as the consumer/patient is intelligently guided to take photos of their dentition. The one or more photos captured at operation 190*a* need not include scan data, height map information, and/or data a clinical scanner uses to stitch together a mesh representation of consumer/patient's dentition. The one or more photos may reflect a state of a treatment plan that is intended for and/or is underway on the consumer/patient. As an example, the one or more photos may capture an initial assessment of the consumer/patient's dentition and/or reflect the patient's progress at a specified stage of a treatment plan. The dental consumer/patient system 102 may store images captured locally, in a networked folder, etc. At an operation 190*b*, the dental consumer/patient system 102 may send captured photos of the consumer/patient to the virtual dental care system 106. This operation may include a file and/or other data transfer over the computer-readable medium 104**.

At an operation **190*c*, the dental professional system 150 may request a first treatment plan for the consumer/patient. In some implementations, a doctor may, through instructions provided to the dental professional system 150, request a first treatment plan for a consumer/patient. The first treatment plan may comprise any set of instructions to address a dental condition of the consumer/patient. As an example, the first treatment plan may include instructions to move a consumer/patient's teeth from a first arrangement toward a target arrangement. The first treatment plan may prescribe use of successive dental appliances (e.g., a plurality of successive aligners shaped to receive and resiliently reposition a consumer/patient's teeth from the initial arrangement toward the target arrangement). The first treatment plan may include restoring attributes of a consumer/patient's dentition using crowns, bridges, implants, and/or other restorative dental appliances. In various implementations, the first treatment plan is based on a clinical scan, such as a clinical scan that occurred before the operation 190*a***.

At an operation **190*d*, the dental professional system 150 may send the request for the first treatment plan to the virtual dental care system 106. This operation may occur as a file and/or data transfer over the computer-readable medium 104**.

At an operation **190*e*, the virtual dental care system 106** may retrieve the first treatment plan in response to the request for the first treatment plan. Retrieving the first treatment plan may involve providing instructions to a treatment datastore to retrieve a clinical data file associated with a consumer/patient. The clinical data file may represent an initial position of the consumer/patient's dentition, an intended target position of the consumer/patient's dentition, and/or a plurality of intermediate positions to move the consumer/patient's dentition from the initial position toward the intended target position. In some implementations, the clinical data file may include specific clinical preferences (stage(s) at which interproximal reduction (IPR) was performed, locations and/or times of application of attachments applied during the first treatment plan, etc.). The clinical data file may also include clinical preferences of the doctor who managed prescription of the first treatment plan as well as specific attributes of dental appliances used to implement the first treatment plan.

At an operation **190*f*, the virtual dental care system 106 may identify an intended arrangement of a first treatment plan at the particular time that the photos of the consumer/patient were taken at the dental consumer/patient system 102. The virtual dental care system 106 may, e.g., use a length of time since initial implementation of the first treatment plan, spatial relationships between teeth in the photos captured at the dental consumer/patient system 102, and/or other information to identify the stage of the first treatment plan at which the photos were captured at the dental consumer/patient system 102. The virtual dental care system 106** may further evaluate a file that represents the intended arrangement of the identified stage of the first treatment plan to identify 3D structures, e.g., meshes corresponding to the identified stage of the first treatment plan.

At an operation 190*g*, the virtual dental care system 106 may evaluate photo parameters of the photos captured at the dental consumer/patient system 102 to generate alignment data, e.g., data representing an alignment of the intended arrangement of the first treatment plan to the photos. In some implementations, the virtual dental care system 106 optimizes 3D parameters from the images captured at the dental consumer/patient system 102. Examples of 3D parameters that may be optimized include camera parameters, location parameters, orientation parameters, etc. 3D parameter optimization may be performed using a variety of techniques, such as differential rendering, expectation maximization, etc. Applicant hereby incorporates by reference the following applications as if set forth fully here: U.S. Pat. App. Ser. No. 62/952,850, U.S. patent application Ser. No. 16/417,354; US Pat. App. Ser. No. 16/400,980; US Pat. App. Ser. No. 16/455,441; and U.S. patent application Ser. No. 14/831,548 (now U.S. patent Ser. No. 10/248,883), U.S. Pat App. Ser. No. 62/705,954, U.S. Pat App. Ser. No. 63/200,432, U.S. patent application Ser. No. 17/443,242, U.S. patent application Ser. No. 17/443,243, U.S. patent application Ser. No. 17/443,244, U.S. patent application Ser. No. 17/443,245, U.S. patent application Ser. No. 17/443,247, U.S. patent application Ser. No. 17/443,248. Once photo parameters are evaluated/optimized, the virtual dental care system 106 may use those photo parameters to determine places where the consumer/patient's teeth are not tracking to the first treatment plan. For instance, the virtual dental care system 106 may evaluate where the consumer/patient's teeth are in intended locations/orientations as well as where teeth deviate from intended locations/orientations.

At an operation 190*h*, the virtual care dental system 106 may generate an alignment mesh (e.g., an updated, segmented mesh) using the alignment data. The alignment mesh may comprise a 3D representation of the consumer/patient's dentition that reflects the photos taken at the consumer/patient system 102. At an operation 190*i*, the virtual care dental system 106 may evaluate the first treatment plan for modifications using the alignment mesh. The virtual dental care system 106 may identify locations where the consumer/patient's teeth are off-track and/or deviating from an intended arrangement prescribed by the first treatment plan. The virtual dental care system 106 may store any modifications in a clinical data file associated with the consumer/patient. At an operation 190*j*, the virtual dental care system 106 may send proposed modifications to a doctor. This operation may occur as a file and/or data transfer over the computer-readable medium 104.

At an operation 190*k*, the dental professional system 150 may present and/or facilitate review of proposed modifications to the doctor. In various implementations, the dental professional system 150 shows a doctor the proposed modifications on a 3D model and/or images representing the consumer/patient's dentition. The dental professional system 150 may further allow the doctor to accept, reject, and/or further modify the 3D model and/or the images. As an example, the dental professional system 150 may allow the doctor to further move positions of attachments, modify aligners and/or force systems, modify stages at which IPR is performed, etc. At an operation 190*l*, the dental professional system 150 may send reviewed modifications to the virtual dental care system 106, e.g., as a file and/or data transfer over the computer-readable medium 104. At an operation 190*m*, the virtual dental care system 106 may update the first treatment plan with the reviewed modifications. In various implementations, the virtual dental care system 106 updates a clinical data file associated with the consumer/patient with the reviewed modifications.

For example, and as will be described in greater detail below, one or more of virtual dental care modules 108 may cause dental consumer/patient system 102, the dental professional system, 150, and/or the virtual dental care system 106 to recite steps of method claims using one or more of FIGS. 5 and/or 8.

Virtual Care

To perform virtual orthodontic care, virtual dental care, and/or other remote medicine, the practitioner may wish to visually inspect the patient. For example, the practitioner may wish to inspect the patient's progress during a treatment plan, diagnose possible issues, and modify the treatment plan as needed. The availability of high-resolution cameras, for instance integrated with smartphones, allows patients to take sufficiently high-resolution photos that may enable the practitioner to inspect patients. For example, an orthodontic practitioner may wish to identify potential issues of appliance fit, and track the appliance fit over time.

As will be described further below, the systems and methods provided in this disclosure may utilize artificial intelligence to provide a practitioner with measurements with respect to appliance fit. The systems and methods provided in this disclosure may improve the functioning of a computing device by more efficiently using image data for assessment, which may further reduce storage requirements and network bandwidth. In addition, the systems and methods provided herein may improve the field of virtual medicine by improving the remote capabilities of practitioners. Moreover, the systems and methods provided herein may improve the field of medical imaging by providing a near-real-time classification of images for various classifiers.

Figure 2:
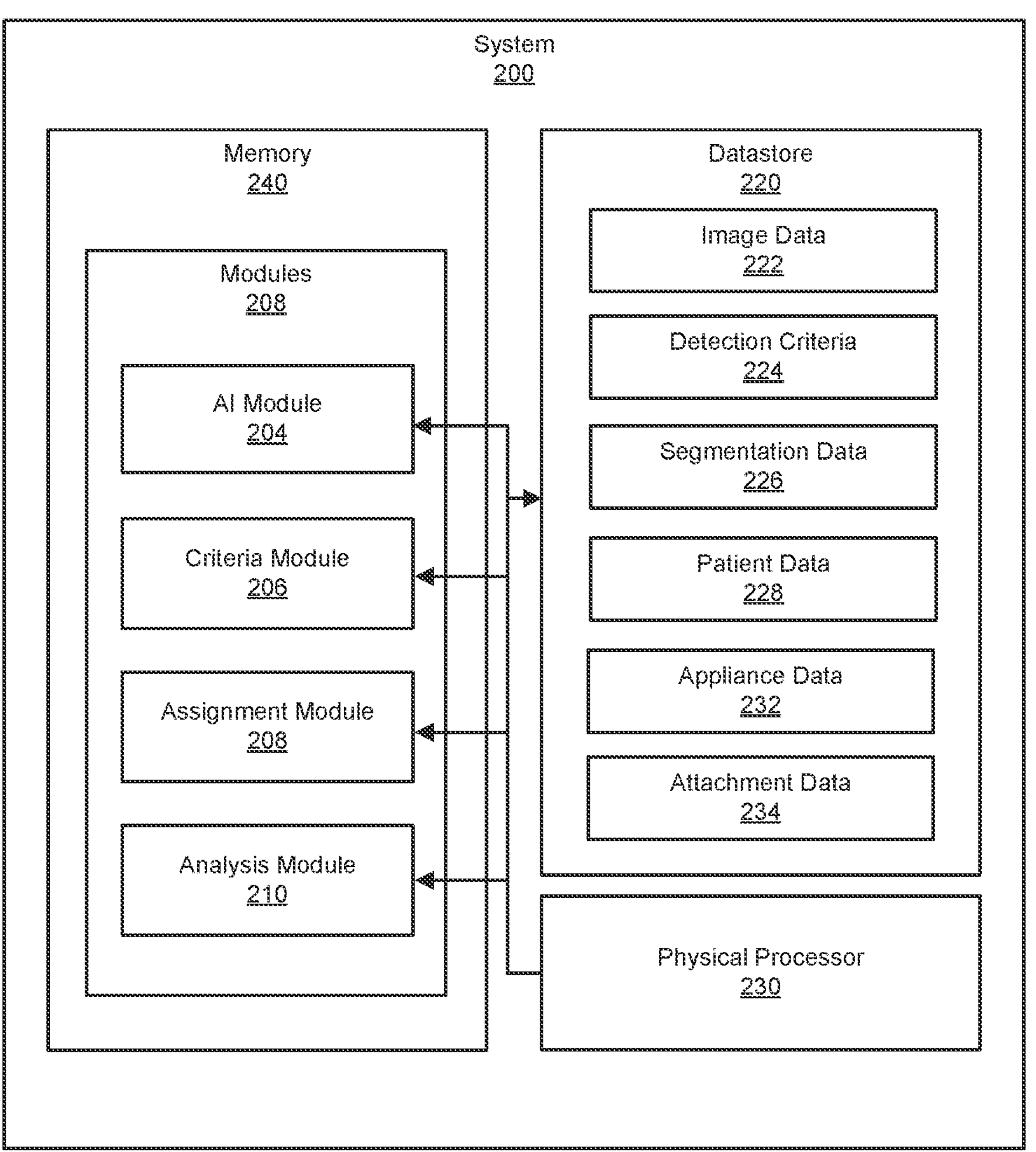
FIG. 2 shows a block diagram of an example system for photo-based assessment, in accordance with some embodiments.

FIG. 2 is a block diagram of an example system 200 for artificial intelligence (AI) assisted photo-based assessment. As illustrated in this figure, example system 200 may include one or more virtual dental care modules 208 for performing one or more tasks. As will be explained in greater detail below, modules 208 may include an AI module 204, a criteria module 206, an assignment module 208, and an analysis module 210. Although illustrated as separate elements, one or more of modules 208 in FIG. 2 may represent portions of a single module or application.

In certain embodiments, one or more of modules 208 in FIG. 2 may represent one or more software applications or programs that, when executed by a computing device, may cause the computing device to perform one or more tasks. For example, and as will be described in greater detail below, one or more of modules 208 may represent modules stored and configured to run on one or more computing devices, such as the devices illustrated in FIG. 1A (e.g., dental consumer/patient system 102 and/or virtual dental care system 106). One or more of modules 208 in FIG. 2 may also represent all or portions of one or more special-purpose computers configured to perform one or more tasks.

As illustrated in FIG. 2, example system 200 may also include one or more virtual dental care datastore(s) 220, such as image data 222, detection criteria 224, segmentation data 226, patient data 228, appliance data 232, and attachment data 234. Virtual dental care datastore(s) 220 may comprise one or more datastores configured to store any type or form of data or information.

Figure 3:
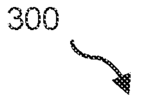
FIG. 3 shows an example user device for photo guidance, in accordance with some embodiments.
Figure 3:
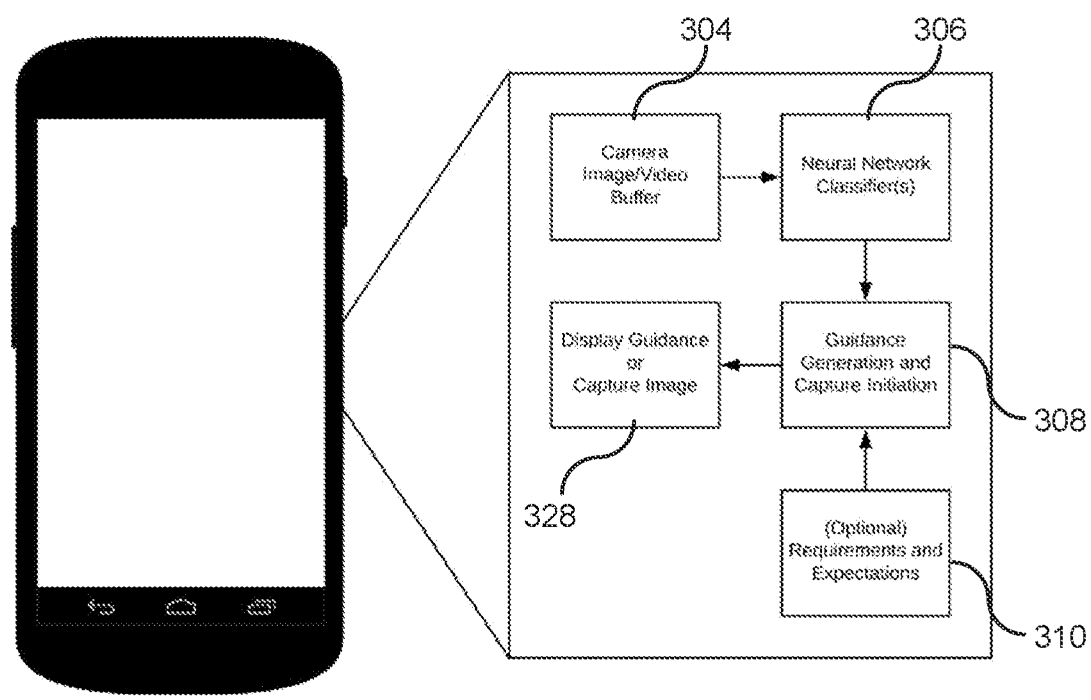

FIG. 3 illustrates data flow of a device 300, which may correspond to system 200 and/or computing device 102. At 304, a camera image/video buffer may temporarily store image data (e.g., image data 222) that may be raw image and/or video data, or may be processed. For example, the image data may be corrected for any visual artefacts, compressed and/or decompressed, reformatted and/or resized for further processing, etc. The image data may include multiple image files, such as multiple photos and/or videos. At 306, image data 222 may be classified by a neural network classifier (e.g., AI module 204).

Figure 4:
FIG. 4 shows an example neural network for photo guidance, in accordance with some embodiments.
Figure 4:
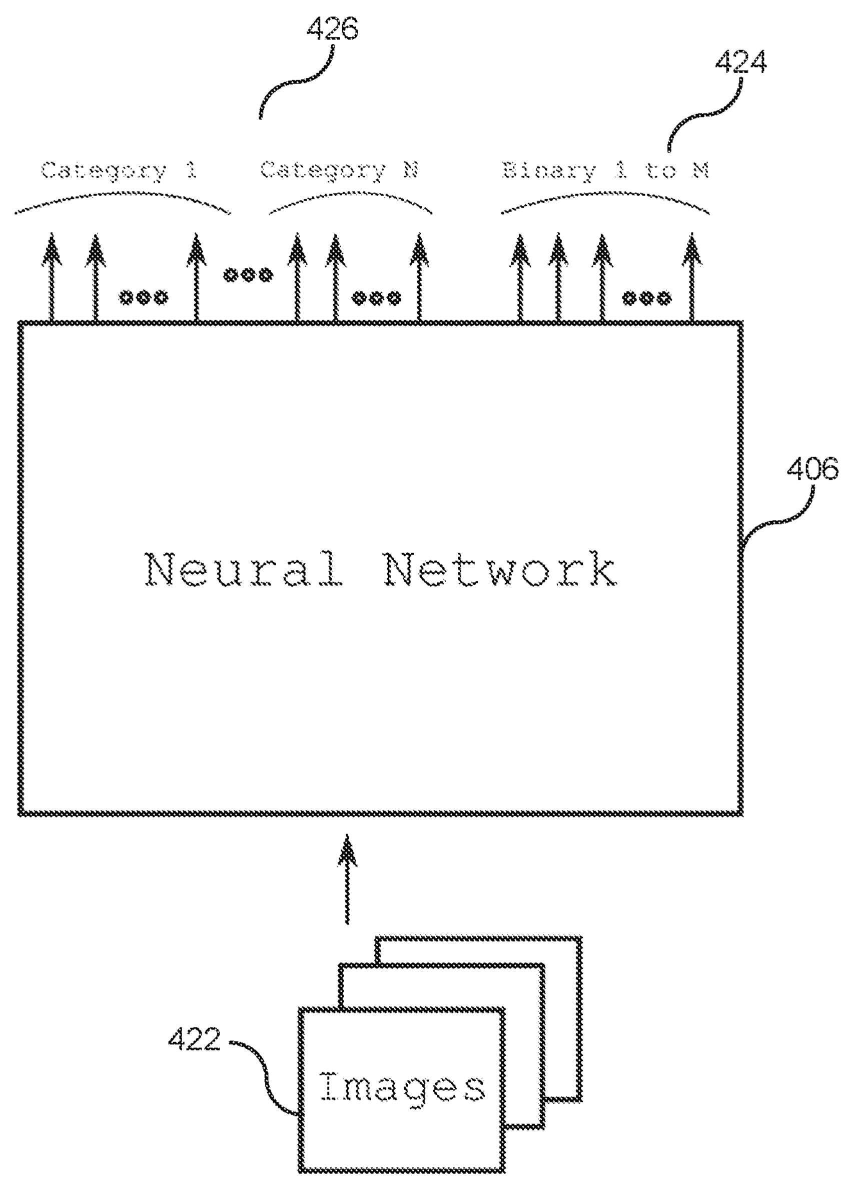

FIG. 4 illustrates an environment 400 for classification using AI and/or machine learning ("ML"). Images 422, which may correspond to image data 222, may be an input to neural network 406, which may correspond to AI module 206. Neural network 406 may include one or more AI schemes, such as a convolutional neural network, deep learning, etc., and may correspond to, for example, MobileNet, EfficientNet, VGG, etc. Neural network 406 may undergo training via training data in order to recognize the various classifications described herein. Neural network 406 may determine categorical classifications 426, which may correspond to various categorical classifications as described herein.

In addition, neural network 406 may include a binary classifier. The binary classifier may determine the binary classifications using binary cross-entropy, which may utilize a loss function to predict a probability of between two possible values for each binary classification. Neural network 406 may determine binary classifications 524, which may correspond to binary classifications described herein.

Turning back to FIG. 3, FIG. 3 illustrates at 310 that requirements and expectations (e.g., detection criteria 224) may be an input for guidance generation and capture initiation at 308. At 328, the guidance may be displayed (e.g., guidance prompts as described herein) or the image may be captured. The guidance prompts may include visual prompts that may be displayed visually, such as an overlay showing guide lines, arrows, graphical instructions, as text in an overlay or window, light patterns, grayed out images, ghost images, etc. The guidance prompts may include audible prompts that may be presented as audio, such as oral instructions, chimes, warning tones, increasing/decreasing beeps (e.g., as the view gets closer/further from satisfying detection criteria 224), etc. The guidance prompts may include haptic prompts that may be presented as vibrations (e.g., of decreasing strength as detection criteria 224 are closer to satisfaction, a vibration when detection criteria 224 are satisfied), warning vibrations, or other haptic responses.

The feedback may include instructions to system 200 for performing automatic actions when detection criteria 224 are not satisfied. The guidance prompts may instruct a camera of system 200 to automatically adjust one or more camera settings. For example, rather than instruction the patient to adjust the camera settings, the camera may automatically make the adjustments. In another example, the guidance prompts may instruct the camera to automatically capture image data 222 if detection criteria 224 are satisfied. Alternatively, automatically capturing image data 222 may include saving portions of an image data stream that satisfies detection criteria 224. In some examples, the guidance prompts may include a confirmation such that the patient may confirm or cancel the automatic actions.

In some examples, the guidance prompts may prevent certain actions, such as preventing capture of image data 222 of the body part when at least one of detection criteria 224 is not satisfied. In some examples, detection criteria 224 may include hardware requirements (e.g., camera resolution, zoom, etc.) such that the guidance prompts may prevent capture of image data 222 if the hardware requirements are not satisfied. In some examples, the guidance prompts may include sending a notification. System 200 may send a notification to server 106 or other computing device to inform the practitioner of certain results. For instance, the notification may indicate if an attachment has fallen off of a tooth, that a plaque buildup is detected, or other abnormal condition that may be highlighted for the practitioner.

As described above, a patient may have a device, such as a smartphone, that is capable of taking photos. The smartphone may be provided a previously-trained neural network that may assist the patient in taking clinically relevant photos. The patient may be provided guidance to ensure the photos satisfy clinical requirements. The requirements may be customized to the patient at that particular stage of the patient's treatment. Thus, the patient's doctor may be able to remotely view the patient to track the patient's progress, update the treatment, or diagnose any issues.

Virtual Care—Aligner Fit

As described herein, using tele-orthodontics or a virtual care system, patients may take their own photographs of their own dentition and send these photographs to their doctor. The doctor may then assess patients' progress toward treatment goals. As described herein, the doctor may assess patients' actual dentitions via photographs and the virtual care system. However, patients and doctors may wish to use tele-orthodontics for assessing orthodontic appliances, such as assessing "aligner fit" for assessing the quality of seating of an aligner on the patient's dentition.

When using a clear aligner for a patient's treatment, aspects of aligner fit may be visible from photographs taken by the patient. As described further herein, the present disclosure provides systems and methods for remote assessment of the quality of seating for clear aligners.

Figure 5:
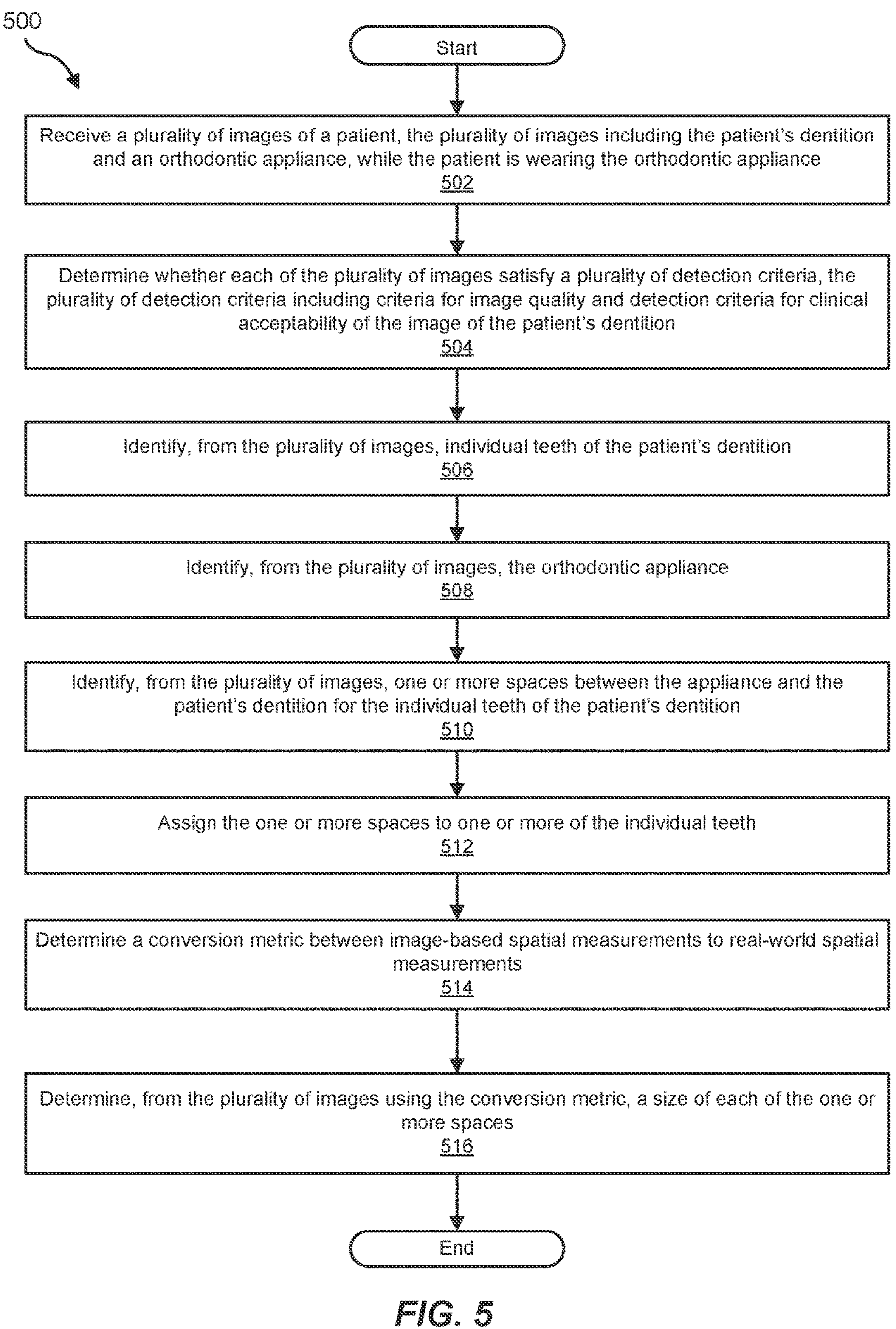
FIG. 5 shows a flow diagram of an example method for determining orthodontic appliance fit, in accordance with some embodiments.

FIG. 5 is a flow diagram of an exemplary computer-implemented method 500 for assessing the quality of seating for clear aligners. The steps shown in FIG. 5 may be performed by any suitable computer-executable code and/or computing system, including the system(s) illustrated in FIGS. 1, 2, and/or 3. In one example, each of the steps shown in FIG. 5 may represent an algorithm whose structure includes and/or is represented by multiple sub-steps, examples of which will be provided in greater detail below.

As illustrated in FIG. 5, at step 502 one or more of the systems described herein may receive a plurality of images of a patient. The plurality of images may include the patient's dentition and an orthodontic appliance, while the patient is wearing the orthodontic appliance. For example, system 200 may receive image data 222 from a camera of system 200 or another camera in communication with system 200.

In some embodiments, the term "image data" may refer to optical capture data which may be temporarily stored in a buffer (e.g., a camera buffer) or otherwise saved in a device memory. Examples of image data include, without limitation, one or more photos, video, etc. Image data may include additional sensor data, such as depth data.

The systems described herein may perform step 502 in a variety of ways. As described herein, the patient may take their own photographs of their own dentition using their own devices (e.g., using dental consumer/patient system 102). This image data may include image data captured with the patient wearing their orthodontic appliance, which may be a clear aligner. The patient may capture the image data during a middle or near an end of a treatment stage, although the patient may capture the image data at any time. Thus, image data 222 may include one or more two-dimensional (2D)

digital photos. For example, FIG. 6A illustrates image data 600 of a patient's dentition including an orthodontic appliance.

Returning to FIG. 5, at step 504 one or more of the systems described herein may determine whether each of the plurality of images satisfy a plurality of detection criteria. The plurality of detection criteria may include criteria for image quality and detection criteria for clinical acceptability of the image of the patient's dentition. For example, criteria module 206 may determine whether image data 222 satisfies detection criteria 224.

The systems described herein may perform step 504 in a variety of ways. In one example, criteria module 206 may use AI and/or ML for checking detection criteria 224. Criteria module 206 may correspond to neural network 406, which may further correspond to AI module 204 described further below. Detection criteria 224 may include various criteria for image quality and/or criteria for clinical acceptability.

The criteria for image quality may ensure that computer vision (e.g., object recognition or segmentation performed by AI module 204 as described herein) may be performed on image data 222. In one example, the criteria for image quality may include criteria for image exposure. The criteria for image exposure may include criteria for determining that the image is bright enough to distinguish the teeth and the aligner. The criteria for image exposure may also include criteria for determining that the image is not so dark that the teeth and the aligner are not distinguishable from each other.

In some examples, the criteria for image quality may include criteria for image sharpness or image blurriness. For instance, the criteria for image sharpness or image blurriness may include criteria for determining that the image is sufficiently sharp to distinguish the teeth and the aligner. The criteria for image sharpness or image blurriness may also include criteria for determining that the image is not so blurry that the teeth and the aligner are not distinguishable from each other.

In some examples, the criteria for image quality may further include criteria for image contrast. The criteria for contrast may include criteria for determining that the image has sufficient contrast to distinguish the teeth and the aligner. The criteria for contrast may also include criteria determining that the contrast is not so low that the teeth and the aligner are not distinguishable from each other.

The criteria for clinical acceptability (or clinical relevance as described herein) may ensure that image data 222 includes sufficient image data of the patient for assessment analysis. In one example, the detection criteria for clinical acceptability of the image of the patient's dentition may include criteria for determining whether or not cheek retractors or a scanning box (with cheek retractors) coupled to a cell phone were used during the image capture process. The presence of cheek retractors (e.g., cheek retractors 650 in FIG. 6A, see also cheek retractors 950 in FIG. 9A) may be indicative of the patient's dentition being sufficiently visible in image data 222. Criteria module 206 may determine if cheek retractors are present in image data 222. In some examples, criteria module 206 may determine whether or not cheek retractors were used during the image capture process based on lip shape. As shown in FIG. 6A, a shape of lips 652 may indicate that cheek retractors 650 were used. For instance, the shape of lips 652 may include a flat shape that may not normally be achievable without cheek retractors 650.

In some examples, the detection criteria for clinical acceptability of the image of the patient's dentition may include determining whether posterior teeth of the patient's dentition are present in the image. For example, criteria module 206 may determine if the patient's posterior teeth (e.g., upper arch teeth 654 and/or lower arch teeth 656 shown in FIG. 6A) are identified in image data 222.

In some examples, the detection criteria for clinical acceptability of the image of the patient's dentition may include a criteria for determining the patient's bite is open in the image. For instance, the detection criteria for clinical acceptability of the image of the patient's dentition may include a criteria for determining the patient's bite is open sufficiently that teeth of the upper arch are not in contact with teeth of the lower arch. Additionally and/or alternatively, the detection criteria for clinical acceptability of the image of the patient's dentition may include a criteria for determining the patient's bite is sufficiently open that the aligner spaces on the upper and lower jaw are distinguishable in the image. As shown in FIG. 6A, upper arch teeth 654 may not be in contact with lower arch teeth 656.

In some examples, criteria module 206 may determine that image data 222 fails to satisfy all detection criteria 224. Criteria module 206 may select a subset of the images that fail one or more detection criteria such that system 200 may provide an indication to a dental professional that the subset of images fail one or more detention criteria. The dental professional may request updated images from the patient, may proceed only with images that satisfy the detection criteria, and/or may continue to proceed with images that fail the detection criteria. Thus, as will be described further below, system 200 may receive a clinical assessment of aligner fit from the dental professional based on the subset of images.

In some examples, criteria module 206 may check detection criteria 224 using classifiers, such as ML classifiers for binary classification and/or categorical classification. In some embodiments, the term "binary classification" may refer to characteristics that may be defined as having one of two states (e.g., yes or no). With respect to the image data, examples of binary classifications may include, without limitation, whether a particular tooth is visible, whether a particular group of teeth are visible (e.g., posterior teeth, etc.), whether an upper jaw is visible, whether a lower jaw is visible, whether an appliance (e.g., an aligner, a cheek retractor, a scanning box, etc.) is visible, whether a focal distance threshold—corresponding to whether an entirety of the body part is visible—is satisfied, whether upper and lower teeth contact, whether a lighting threshold is satisfied, whether a localized calculus (e.g., plaque buildup) is present, whether a gingiva recession is present, and other examples described herein.

In some embodiments, the term "categorical classification" may refer to characteristics that may be classified into one or more categories. In some implementations, the characteristics may be classified into one or more sets of mutually exclusive categories. With respect to the image data, examples of categorical classifications may include, without limitation, an anterior view, a left buccal view, a right buccal view, and other examples described herein.

In some embodiments, certain characteristics may be either binary or categorical classifications. For example, a head pose of the patient (e.g., an angle of the patient's head as viewed in the image data stream) may be a binary classification (e.g., upright or tilted) or a categorical classification (e.g., classified into various pose categories based on slight tilt, large tilt, angle toward or away, etc.). In another example, a blurriness of the image data stream may be either a binary classification (e.g., too blurry or not too blurry) or a categorical classification (e.g., a degree of blurriness, an area within the image data stream being blurry).

In some examples, detection criteria 224 may reside in in virtual dental care system 106 (which may be predetermined by a practitioner) such that detection criteria 224 may be sent to dental consumer/patient system 102. In other examples, virtual dental care system 106 may send patient data 136 and/or treatment data 138 to dental consumer/patient system 102 such that dental consumer/patient system 102 may locally determine detection criteria 224.

Turning back to FIG. 5, at step 506 one or more of the systems described herein may identify, from the plurality of images, individual teeth of the patient's dentition. For example, AI module 204, which may correspond to neural network 406, may use computer vision and/or object recognition on image data 222 to identify the individual teeth from image data 222, the results of which may be stored in segmentation data 226.

The systems described herein may perform step 506 in a variety of ways. In one example, AI module 204 may identify individual teeth of the patient's dentition by segmenting the teeth in image data 222.

In one example, semantic segmentation may be performed to classify each pixel of the image data into one of a plurality of classes. For example, a probability of belonging to each class may be determined for each pixel of the image data. Each pixel may be classified based on which class the pixel has the highest probability of matching. The classes may include, for example, a tooth class indicating the patient's teeth (which may be portions of the teeth, either covered or not covered by the orthodontic appliance), a gap class indicating a gap between the orthodontic appliance and a corresponding gingival edge, and a space class indicating a space between an incisal or occlusal edge of the orthodontic appliance, such as an incisal edge of an external surface of the appliance or an internal edge, such as an internal incisal or occlusal edge of a tooth receive cavity, and an incisal or occlusal edge of a corresponding tooth. In other examples, other classes may be used, such as a gum class corresponding to the patient's gums, an appliance class, other classes, etc. By performing the semantic segmentation, pixels corresponding to the orthodontic appliance (e.g., based on the gap class and the space class) may be distinguished from pixels corresponding to the patient's dentition without the appliance (e.g., the tooth class). As will be described further below, the gap class and/or the space class may also correspond to a misalignment.

In some examples, the semantic segmentation may be performed using machine learning. For example, neural network 406 or other machine learning scheme may be used to perform the semantic segmentation. In some example, neural network 406 may be trained to perform the semantic segmentation by inputting an image data set, such as a training data set, for semantic segmentation by the neural network. This training data set may have a corresponding mask data set of the desired semantic segmentation. The training may further include computing an error between an output of the neural network (e.g. by performing the semantic segmentation) and the mask data set corresponding to the image data set, and adjusting the parameters of neural network 406 to reduce the error.

In some examples, the various segmentation schemes described herein may be applied per tooth such that different segmentation schemes may be applied to different identified teeth. By identifying tooth-to-tooth boundaries, each tooth may be analyzed to provide tooth-specific information or data. For example, color evaluation may be applied per tooth such that color values and/or thresholds may be local to each tooth. Differences in lighting and/or actual differences between tooth colors may affect global color values whereas local tooth color analysis may more readily identify between classes. In another example, semantic segmentation may be applied to identify spaces per tooth. The semantic segmentation scheme may use a semantic segmentation model to find spacing for a given tooth, such as upper-left central incisor, etc. Alternatively, each tooth may be identified in the image data and identified tooth spacing may be associated to the corresponding specific tooth.

Figure 7A:
FIGS. 7A-B show diagrams of mapping individual teeth, in accordance with some embodiments.
Figure 7A:
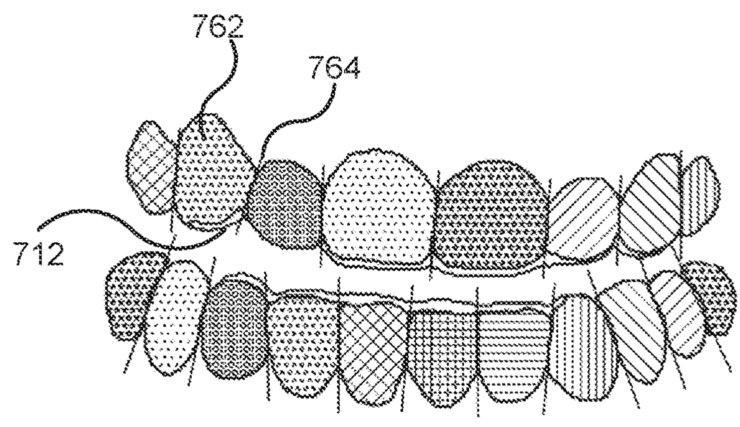

AI module 204 may produce segmentation data 226, which may include data on individual teeth identified in image data 222. FIG. 7 illustrates a segmentation 700 (which may correspond to segmentation data 226), in which AI module 204 has identified each individual tooth 762. Segmentation data 226 may include additional data, such as locations of spaces and assignments of spaces to individual teeth, as will be described further below.

In some embodiments, treatment plan data is used to identify the segmented teeth in the image. The segmentation data may be processed based on the treatment plan to identify and number each tooth. Segmentation without post-processing of the segmented teeth based on the treatment plan may result in misidentified teeth. For example, a patient may be missing teeth which may be identified in the treatment plan, but not during segmentation. Accordingly, the resulting segmentation and segmentation data may be required to not conflict with or conform with the teeth that are present in the treatment plan. In some embodiments, such as for an adult with all adult teeth, the process may include segmenting the teeth in the image, as discussed herein, and identifying each tooth, such as by numbering the teeth.

The process may then then perform a post-processing step that, if an inconsistency is found, renumbers the teeth to match the teeth in the treatment plan. For example, if the patient was missing the right upper first premolar (tooth 5), but the initial tooth segmentation showed that the image had teeth 3, 4, 5, 6, 7, and 8—the post processing may renumber the teeth present in the image correctly as 2, 3, 4, 6, 7, and 8, omitting tooth number 5, the right upper first premolar. In a case with primary dentition, the treatment plan may include an eruption compensation feature, such as an location between tooth teeth, an area or a volume identified for a permanent tooth that has not yet erupted. During segmentation postprocessing the tooth numbering results may include or not include a tooth at position.

Returning to FIG. 5, at step 508 one or more of the systems described herein may identify, from the plurality of images, the orthodontic appliance. For example, AI module 204 may identify the orthodontic appliance from image data 222, the results of which may be stored in segmentation data 226.

The systems described herein may perform step 508 in a variety of ways. In some examples, identifying the orthodontic appliance may include evaluating a color value of each pixel to identify a tooth portion without the orthodontic appliance and a tooth portion with the orthodontic appliance. For instance, a threshold-based segmentation may be used in which color thresholds corresponding to teeth, gums, appliances over teeth, and appliances without teeth, may be used to classify each pixel.

In other examples, identifying the orthodontic appliance may include applying one or more filters to the image data to determine a tooth edge and an orthodontic appliance edge.

For instance, an edge-based segmentation may be used to find edges and regions inside the edges may be designated by class based on color features, such as the color threshold described herein.

At step 510 one or more of the systems described herein may identify, from the plurality of images, one or more spaces between the appliance and the patient's dentition for the individual teeth of the patient's dentition. For example, AI module 204 may identify spaces between the identified appliance and the identified individual teeth from image data 222, the results of which may be stored in segmentation data 226.

The systems described herein may perform step 510 in a variety of ways. In one example, semantic segmentation may be performed to classify each pixel of the image data into one of a plurality of classes. For example, a probability of belonging to each class may be determined for each pixel of the image data. Each pixel may be classified based on which class the pixel has the highest probability of matching. The classes may include, for example, a space class indicating a space between an incisal or occlusal edge of the orthodontic appliance and a corresponding incisal or occlusal edge of a corresponding tooth. By performing the semantic segmentation, pixels corresponding to the space class may be identified.

In some examples, the semantic segmentation may be performed using machine learning. For example, neural network 406 or other machine learning scheme may be used to perform the semantic segmentation. In some example, neural network 406 may be trained to perform the semantic segmentation by inputting an image data set, such as a training data set, for semantic segmentation by the neural network. This training data set may have a corresponding mask data set of the desired semantic segmentation. The training may further include computing an error between an output of the neural network (e.g. by performing the semantic segmentation) and the mask data set corresponding to the image data set, and adjusting the parameters of neural network 406 to reduce the error.

In some examples, the various segmentation schemes described herein may be applied per tooth such that different segmentation schemes may be applied to different identified teeth. For example, semantic segmentation may be applied to identify spaces per tooth. The semantic segmentation scheme may use a semantic segmentation model to find spacing for a given tooth, such as upper-left central incisor, etc. Alternatively, each tooth may be identified in the image data and identified tooth spacing may be associated to the corresponding specific tooth.

FIGS. 6B and 6C illustrate image data 602 and mask data 604 in which semantic segmentation has identified a gap region 610, a space region 620, and a space region 630. In FIG. 6B mask data 604 is overlaid onto image data 600 (in FIG. 6A) to better show how semantic segmentation may produce mask data 604.

Returning to FIG. 5, at step 512 one or more of the systems described herein may assign the one or more spaces to one or more of the individual teeth. For example, assignment module 208 may assign the identified spaces to corresponding individual teeth, the results of which may be stored in segmentation data 226.

The systems described herein may perform step 512 in a variety of ways. In one example, assignment module 208 may assign each pixel identified as aligner space to a tooth. FIG. 7A illustrates an aligner space 712 that AI module 204 may have previously identified using methods described herein. In some examples, assigning each pixel identified as aligner space to a tooth may include determining a boundary for a tooth between each adjacent tooth, extending the boundary beyond the end of the tooth, and assigning the aligner space between the boundary lines to the corresponding tooth, such as between adjacent boundary lines. For instance, in FIG. 7A, a tooth boundary 764 corresponding to tooth 762 may be extended such that aligner space 712 may be located between tooth boundaries 764 of tooth 762. Assignment module 208 may therefore assign aligner space 712 to tooth 762.

Figure 7B:
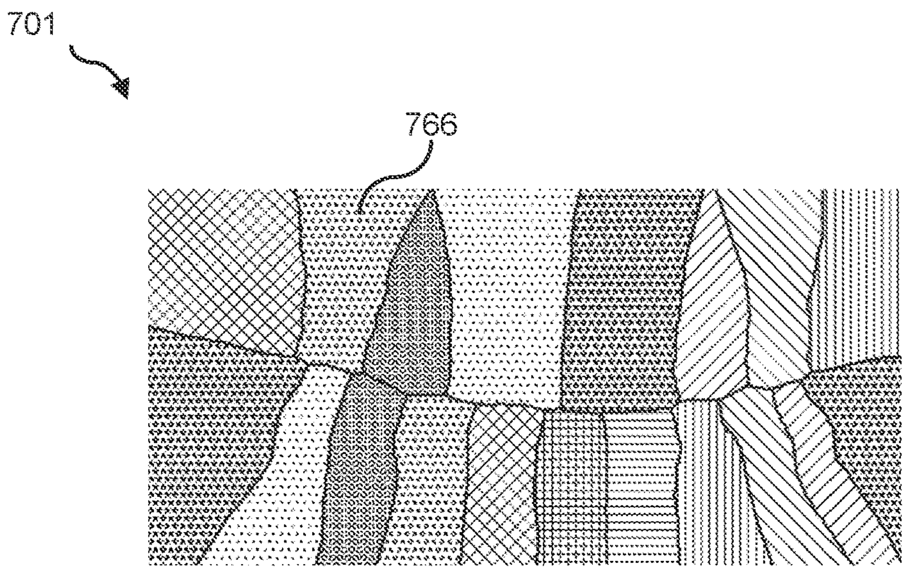

In some examples, assigning each pixel identified as aligner space to a tooth may include using a distance transform for each pixel to find the distance of each pixel to the nearest tooth, and assigning the pixel to the nearest tooth. FIG. 7B illustrates a distance map 701 corresponding to segmentation 700. Based on tooth boundaries (e.g., tooth boundary 764), assignment module 208 may divide distance map 701 into various tooth regions 766 corresponding to each individual tooth. Each pixel within each tooth region 766 may have an associated distance value of a distance between the pixel and the nearest tooth pixel (e.g., by determining vectors from a given pixel to each tooth edge pixel and selecting the smallest magnitude of the vectors). Therefore, pixels corresponding to tooth pixels may have a value of 0, and the distance values may increase for pixels located away from the nearest tooth pixel. In FIGS. 7A and 7B, the pixels for aligner space 712 may have the smallest distance values to tooth 762 (as compared to other teeth) such that assignment module 208 may assign aligner space 712 to tooth 762.

The distances may be measured using image-based spatial measurements (e.g., pixels) or may use real-world spatial measurements based on a conversion metric described further below.

In some embodiments, the treatment plan may be used to identify intentional spaces between the aligner and the patient's teeth. For example, when teeth are tipped or moved during treatment, an aligner may have a space formed therein to accommodate the movement of the tooth during a stage of the treatment plan. In some planned tooth movements, an intentional space is left in the aligner to avoid interfering in the movement. These spaces have known sizes that may be determined or stored with the treatment plan. The space may be defied as a volume or area adjacent a tooth or between adjacent teeth. When such planned-space features are detected in the treatment plan, the result of the aligner fit algorithm can be adjusted to account for these spaces. For example, if the treatment plan includes information regarding the existence of a space, such as a volume of the space or a projected area of the space and a corresponding space is identified during segmentation (or otherwise) the process may identify the space in the image as intentional space and not include that in the space mask or when determining aligner fit, or otherwise ignore that intentional space when determining space between the aligner and the teeth. For example, the planned space may be subtracted off the found space in order to arrive at the amount of aligner space that is due to poor aligner fit.

Figure 6D:
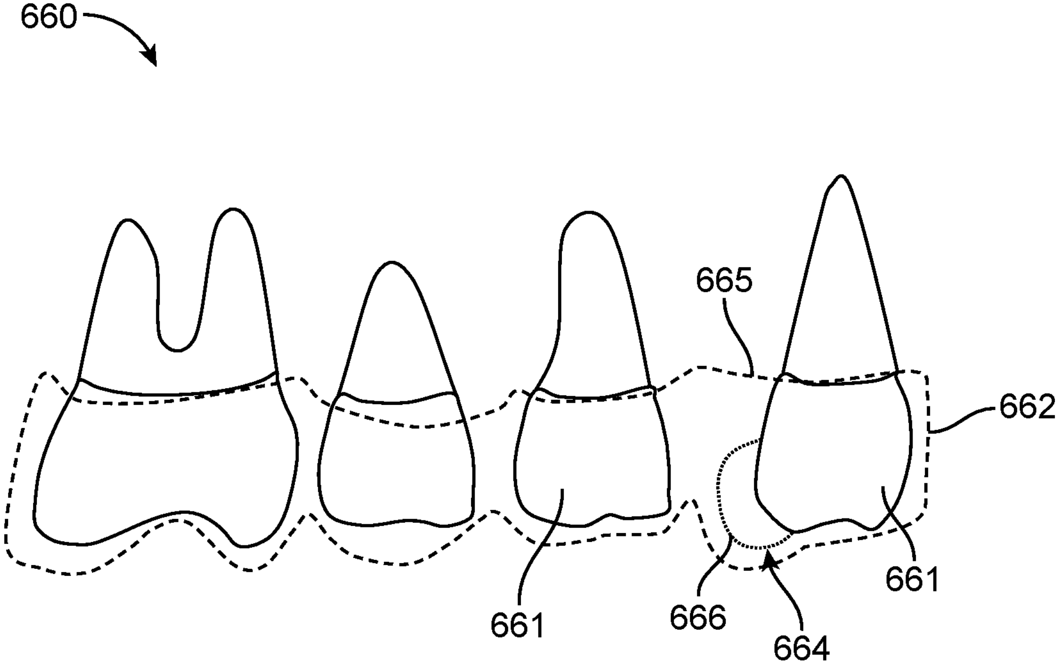

FIG. 6D depicts an image 660 in which teeth 661, an aligner 662, and a space 664 between adjacent teeth have been identified. A portion 666 of the space 664 is determined to be a planned or intentional space 666. The space between the occlusal surface of the planned or intentional space 666 and the aligner is used to determine the amount of aligner space that is due to poor aligner fit. The space between the planned or intentional space 666 and a gingival portion of the aligner may be ignored.

When is extracted, or expected to be erupting, or otherwise known to be missing, an aligner may have a space formed therein to accommodate the eruption of the tooth or the missing tooth during a stage of the treatment plan. The erupting or missing tooth spaces have known sizes that may be determined or stored with the treatment plan. The space may be defied as a volume or area. When such missing or erupting teeth are detected in the treatment plan, the result of the aligner fit algorithm can be adjusted to account for these spaces. For example, if the treatment plan includes information regarding the existence of the space of the erupting tooth, such as a volume of the space or a projected area of the space and a corresponding space is identified during segmentation (or otherwise) in a patient image, the process may identify the space in the image as intentional space and not include that space in the space mask or when determining aligner fit, or otherwise ignore that intentional space when determining space between the aligner and the teeth. For example, the planned space may be subtracted off the found space in order to arrive at the amount of aligner space that is due to poor aligner fit.

Figure 6E:
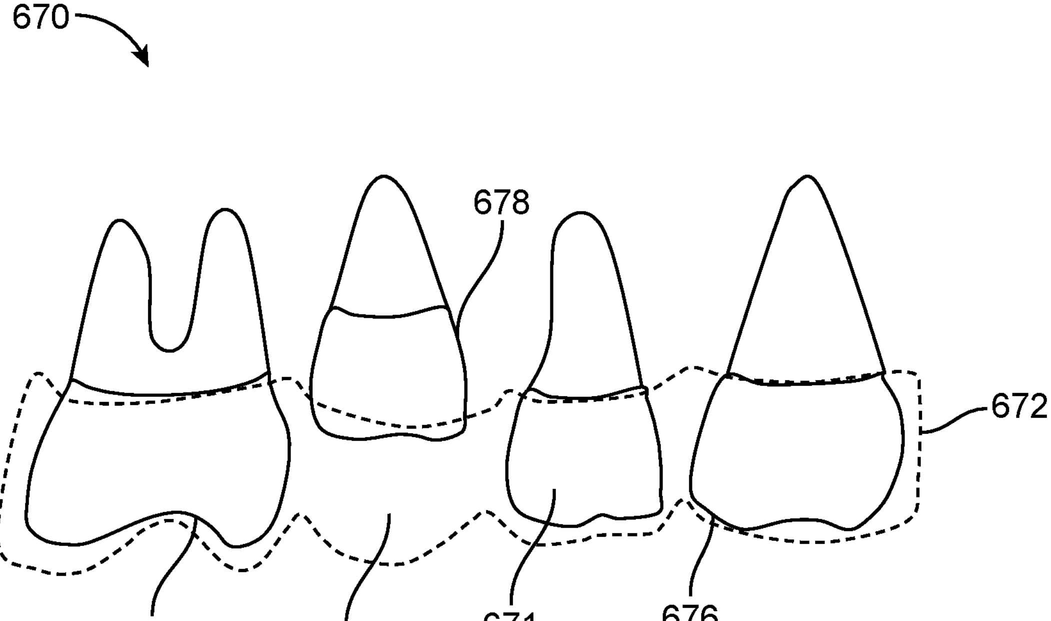

FIG. 6E depicts an image 670 in which teeth 671, an aligner 672, and a space 674 for an erupting tooth 678 have been identified. The space 674 is determined to be a planned or intentional space to accommodate the eruption of the tooth. This intentional space is ignored in order to determine the amount of aligner space that is due to poor aligner fit. In some embodiments, any space associated with an erupting tooth may be ignored.

Returning to FIG. 5, at step 514 one or more of the systems described herein may determine a conversion metric between image-based spatial measurements to real-world spatial measurements. For example, analysis module 210 may determine a conversion metric using one or more of image data 222, segmentation data 226, and patient data 228, the results of which may be stored in appliance data 232.

Although image-based spatial measurements (e.g., pixel heights) may be used for assessment, in some examples, the pixel height may be converted to a standard unit of measurement. For instance, the patient's doctor may prefer to see misalignment heights measured in millimeters or other unit of measurement.

The systems described herein may perform step 514 in a variety of ways. In one example, analysis module 210 may determine a conversion metric between image-based spatial measurements to real-world spatial measurements by determining a conversion from image size to real-world size based on the relationship between the real-world size of the patient's teeth from a patient's treatment plan and an image size of the patient's teeth in the image. In some examples, the conversion may correspond to a pixel dimension, such as a pixel's length and/or width that may be measured from image data 222. To convert the pixel measurement, a reference object, which may be an identifiable may be identified from the image data. The reference object may be selected based on having an available known measurement for a real-world size of the patient's teeth.

In some examples, the real-world size of the patient's teeth from a patient's treatment plan may be from a three-dimensional model of the patient's teeth. For instance, patient data 228 (which may correspond to patient data 136 and/or treatment data 138) may include a 3D model of the patient's teeth that may include real-world measurements of the patient's teeth. Additionally and/or alternatively, patient data 228 may include measurements taken of the patient's teeth.

In some examples, the relationship between the real-world size of the patient's teeth from a patient's treatment plan and an image size of the patient's teeth in the image may correspond to a relationship between the width of the teeth, the length of the facial-axis of the clinical crown (FACC), and/or the overall tooth area, of each of a set of the patient's teeth (such as the patient's incisors) in the treatment plan and each corresponding teeth in the image. For example, analysis module 210 may determine the length of the patient's incisors from patient data 228 to determine the conversion metric. A pixel height of the incisor may be determined from the image data (for example by determining edges for the identified incisor and counting pixels along a desired dimension) and used with the incisor measurement to determine a conversion factor between pixels and the standard unit of measurement (e.g., mm).

Because image data 222 may include images of the patient's dentition taken at an angle (e.g., skewed rather than perfectly aligned with pixel axes), analysis module 210 may apply corrections to produce a more accurate conversion metric. For instance, analysis module 210 may project a tooth from the treatment plan into a plane that corresponds to a plane of a corresponding tooth in the image. Another correction may include subtracting the identified aligner space from the segmented teeth in the images to ensure more accurate tooth edges. Because patients may often take photos from an elevated perspective using their device, in some examples upper arch teeth may have less thickness whereas lower arch teeth may have more thickness.

In some other examples, the conversion factor may be determined using a global average of pixels-per-tooth of all identified teeth, optionally excluding outlier values. In yet other examples, the conversion factor may be determined by constructing a field of pixel-to-mm sizes over an entirety of the image data and interpolating and/or extrapolating pixel-to-mm sizes across the identified arch.

At step 516 one or more of the systems described herein may determine, from the plurality of images using the conversion metric, a size of each of the one or more spaces. For example, analysis module 210 may determine, from image data 222 using the conversion metric, sizes of each identified space, the results of which may be stored in appliance data 232.

The systems described herein may perform step 516 in a variety of ways. In one example, analysis module 210 may determine the size of each of the aligner space for each tooth based on the largest distance between an aligner space pixel and the respective tooth. In some examples, analysis module 210 may use a largest distance from pixels of aligner space 712 from distance map 701 as the size of aligner space 712.

For example, analysis module 210 may, for each aligner space (e.g., from each image), identify a vertical orientation of teeth in the corresponding image. Based on the patient's pose when taking photos, the vertical orientation of teeth may not align with pixel orientation and may be offset by an angle. Analysis module 210 may then measure a largest number of pixels of aligner space in the vertical dimension between respective tooth boundary lines. For instance, analysis module 210 may break the aligner space spanning between the boundary lines into tooth-aligned pixel columns along the identified vertical orientation (e.g., along the angle). Analysis module 210 may then measure a number of pixels for each tooth-aligned pixel column (which may include fractional pixel counts) and take the largest value from the tooth-aligned pixel columns. Analysis module 210 may then convert this largest number of pixels into a real-world spatial size using the conversion metric.

In some examples, an aggregate value may be used. As seen in FIG. 7A, each aligner space may include a range of pixels, such as across a horizontal range across the corresponding tooth. In such examples, the aligner space size (e.g., height, length, and/or width) may be calculated from aggregating the pixels. For example, for aligner space 7A, the aligner space size may be calculated using, for example, an 80th percentile value of the distances associated with the various pixels, although in other examples, other percentiles may be used such that outlier values may not significantly impact the aligner space size. Alternatively, other aggregating functions, such as average, mode, etc. may be used.

In some examples, the aligner space size may be further adjusted. The semantic segmentation may underestimate aligner spaces. In such instances, a thickness offset (e.g., 0.4-0.8 mm) may be added from the calculated aligner space size to account for a material thickness of the orthodontic appliance. The thickness offset may be obtained from a treatment plan for the patient.

The semantic segmentation may overestimate aligner spaces. In such instances, a thickness offset (e.g., 0.4-0.8 mm) may be subtracted from the calculated aligner space size to account for a material thickness of the orthodontic appliance. The thickness offset may be obtained from a treatment plan for the patient.

In some examples, system 200 may enable tracking aligner spaces over time, which may be stored in appliance data 232. For example, system 200 may receive a second plurality of images of the patient, determine, from the second plurality of images, a second size of each of the one or more spaces, and determine that the aligner space is increase or decreasing over time based on the first size and the second size. For example, the patient may capture image data at various points in time during a treatment stage. A misalignment trend may be identified from the tracked sizes. The misalignment trend may be defined as a general trend (e.g., increasing, decreasing, etc.), as height deltas (e.g., the changes in aligner space sizes at each point in time), or by actual aligner space size values.

In some examples, the practitioner and/or patient may be notified in response to certain aligner space sizes and/or trends. In one example, a misalignment threshold may comprise a plurality of misalignment thresholds. For example, 0.5 mm space may not be desirable but may not necessarily require corrective action and therefore may be set as a low threshold. However, 0.75 mm may require corrective action and thus be set as a high threshold. In some examples, if the misalignment trend is tracked, the misalignment threshold may include a misalignment trend threshold. For example, if the misalignment height remains at 0.75 mm at multiple points of time, corrective action may be needed.

In one example, the notification may include a message or other notification to the patient's doctor. In some examples, the notification may include providing a visual overlay of the misalignment, as in FIG. 6B. In some examples, a color may indicate a type of misalignment.

In some examples, if the misalignment threshold includes a plurality of misalignment thresholds, the notification may include increasing priority based on the threshold met. For each range between the multiple thresholds, a different color may be used when depicting mask data. For example, if the misalignment height is below a low threshold, a low priority color such as blue may be used. If between the low and high threshold, a low warning color such as yellow may be used. If exceeding the high threshold, a high warning color such as orange may be used.

In some examples, the misalignment threshold may include the misalignment trend threshold. The notification may be provided in response to satisfying the misalignment trend threshold.

Although method 500 is presented as a sequence of steps, in some examples, the steps of method 500 may be repeated as needed to provide continuous feedback, improve assessment, and/or track changes over time. Thus, certain steps may be repeated, and data may be continuously updated.

Although the examples herein are described with respect to orthodontic care, in other implementations the remote care may include any other medical care that may be conducted via external photography.

Attachment Detection

As part of a patient's treatment, a patient may wear an orthodontic appliance for repositioning one or more teeth. Teeth that are moved may also serve as a base or anchor for holding the appliance as it is worn by the patient. In some cases, no wires or other means will be provided for holding an appliance in place over the teeth. In some cases, however, it may be desirable or necessary to provide individual attachments or other anchoring elements on the patient's teeth, with corresponding receptacles or apertures in the appliance so that the appliance can apply a selected force on the tooth. Exemplary appliances, including those utilized in the Invisalign® System, are described in numerous patents and patent applications assigned to Align Technology, Inc. including, for example, in U.S. Pat. Nos. 6,450,807, and 5,975,893, as well as on the company's website, which is accessible on the World Wide Web (see, e.g., the URL "invisalign.com"). Examples of tooth-mounted attachments suitable for use with orthodontic appliances are also described in patents and patent applications assigned to Align Technology, Inc., including, for example, U.S. Pat. Nos. 6,309,215 and 6,830,450.

Image-based systems and methods as described herein may allow for remote assessment and follow-up with a patient during orthodontic treatment. The systems and methods allow a doctor to quickly and accurately assess a patient's progress or lack thereof based on photos or images the patient has taken. The photos or images to be taken outside the doctor's office or other clinical offices and instead may be taken by, for example, a handheld device such as a smart phone or digital camera. The assessment may include identifying and/or tracking attachments to the patient's teeth during orthodontic treatment.

In some embodiments, the patient captures two-dimensional photographic images of their teeth, which are then compared with three-dimensional models of the expected attachments on the patient's teeth during a given stage of treatment. The comparison may include identifying the presence of attachments and the expected attachments on the patient's teeth based on a three-dimensional model of the patient's teeth for the particular stage of treatment. During some treatment plans, one or more attachments may fall off the patient's teeth. The doctor may wish to confirm whether one or more attachments may require reattachment before calling the patient back to the doctor's office or other clinical offices.

Figure 8:
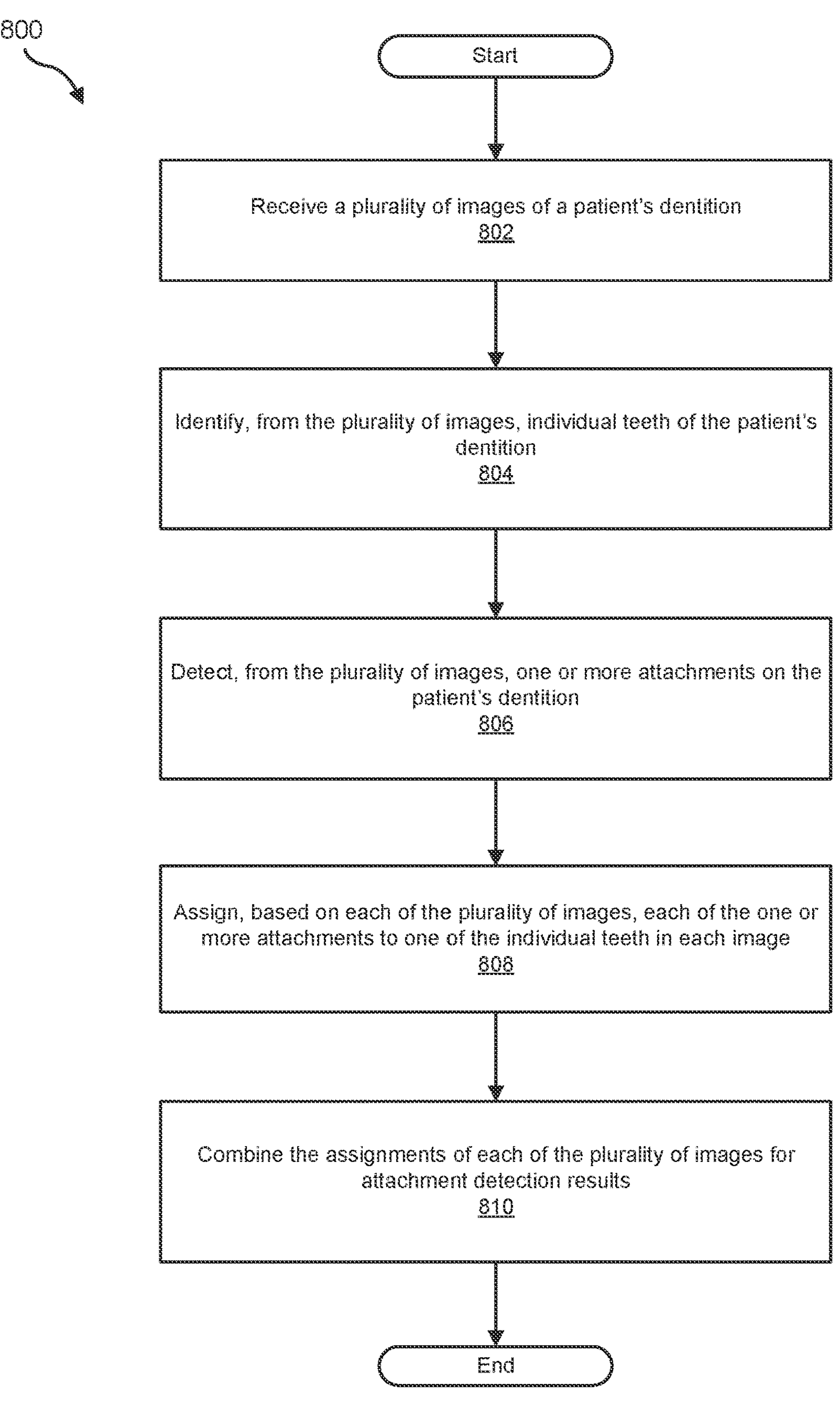
FIG. 8 shows a flow diagram of an example method for attachment detection, in accordance with some embodiments.

FIG. 8 is a flow diagram of an exemplary computer-implemented method 800 for detecting attachments on teeth. The steps shown in FIG. 8 may be performed by any suitable computer-executable code and/or computing system, including the system(s) illustrated in FIGS. 1, 2, and/or 3. In one example, each of the steps shown in FIG. 8 may represent an algorithm whose structure includes and/or is represented by multiple sub-steps, examples of which will be provided in greater detail below.

As illustrated in FIG. 8, at step 802 one or more of the systems described herein may receive a plurality of images of a patient's dentition. The plurality of images may include the patient's dentition without an orthodontic appliance. For example, system 200 may receive image data 222 from a camera of system 200 or another camera in communication with system 200. As described herein, the patient may take photos using their own device.

The systems described herein may perform step 802 in a variety of ways. In one example, the plurality of images may include images with the arches in open-bite (see, e.g., FIG. 6A). In one example, the plurality of images may include images with the arches in closed-bite (see, e.g., FIG. 9A). In one example, the plurality of images may include an anterior image with the arches in open-bite, a left lateral image with the arches in open-bite, a right lateral image with the arches in open-bite, an anterior image with the arches in closed-bite, a left lateral image with the arches in closed-bite, and a right lateral image with the arches in closed-bite.

In some examples, criteria module 206 may further check image data 222 for detection criteria 224, as described herein.

At step 804 one or more of the systems described herein may identify, from the plurality of images, individual teeth of the patient's dentition. For example, AI module 204 may identify individual teeth of the patient's dentition from image data 222, which may be stored in segmentation data 226.

The systems described herein may perform step 804 in a variety of ways. In one example, AI module 204 may perform segmentation to identify individual teeth as described herein. For instance, identifying, from the plurality of images, individual teeth of the patient's dentition may include segmenting the individual teeth of the patient's dentition contained in the image. Segmenting the individual teeth may include determining which teeth are located in the image and which pixels of the image are a part of each tooth. Additionally, identifying individual teeth may also include assigning each identified tooth to a corresponding tooth in a patient's treatment plan (e.g., from patient data 228).

Figures 9A, 9B, 9C:
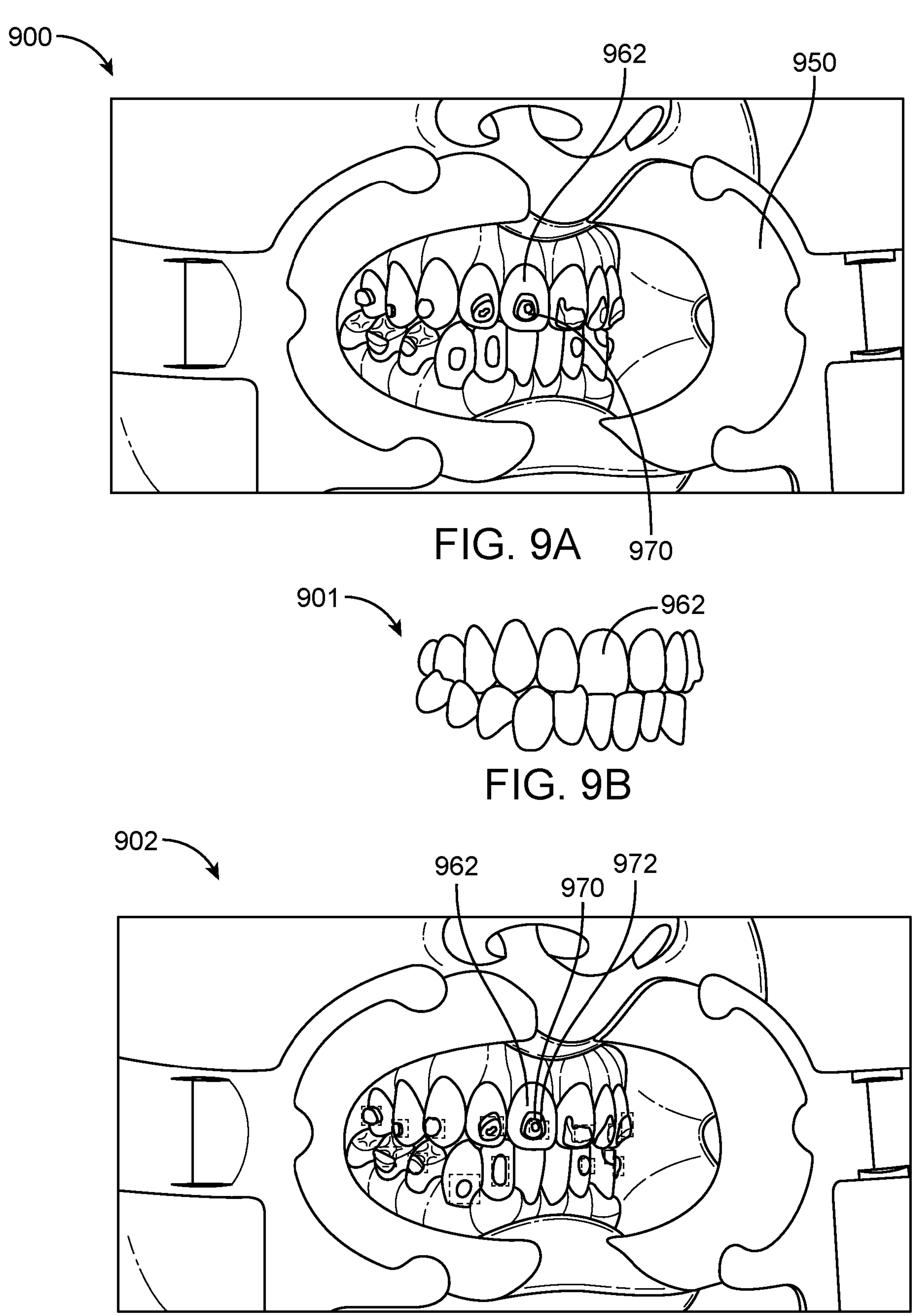
FIGS. 9A-C illustrate detection of attachments, in accordance with some embodiments.

FIGS. 9A-9C illustrate a patient's dentition. Image data 900 (which may correspond to image data 222), shows the one or more of the patient's tooth 962 and attachment 970 being visible. Segmentation 901 in FIG. 9B illustrates identification of individual tooth 992. Processed image data 902 in FIG. 9C illustrates bounding box 972 for attachment 970, as will be further described below.

Turning back to FIG. 8, at step 806 one or more of the systems described herein may detect, from the plurality of images, one or more attachments on the patient's dentition. For example, AI module 204 may detect attachments on the patient's teeth from image data 222, the results of which may be stored in attachment data 234.

The systems described herein may perform step 806 in a variety of ways. In one example, AI module 204 may use computer vision and/or object recognition as described herein. For example, AI module 204 may detect visual changes (e.g., unexpected visual deformations for bare tooth surfaces, detectable structures on tooth surfaces, etc.) in the identified teeth, identify the visual changes as attachments, and form bounding boxes around each detected attachment. A bounding box may define outer boundaries of an identified structure and may be rectangular and/or square in shape to simplify processing, particularly for irregularly shaped objects. FIG. 9C illustrates bounding box 972 for attachment 970.

Returning to FIG. 8, at step 808 one or more of the systems described herein may assign, based on each of the plurality of images, each of the one or more attachments to one of the individual teeth in each image. For example, assignment module 208 may assign each identified attachment from each image of image data 222 to a corresponding tooth identified in the same image, the results of which may be stored in attachment data 234.

The systems described herein may perform step 808 in a variety of ways. In one example, assignment module 208 may assign each of the one or more attachments to one of the individual teeth includes by determining a center point of the attachment bounding box, and assigning the attachment to the tooth based on which the center point is located. In FIG. 9C, a center point of bounding box 972 may be located on tooth 962 such that bounding box 972, and attachment 970 corresponding thereto, to tooth 962.

In some examples, assignment module 208 may assign each of the one or more attachments to one of the individual teeth includes by determining the area of each tooth within the bounding box, and assigning the attachment to the tooth based on which tooth has the greatest area within the bounding box. In FIG. 9C, tooth 962 may have the greatest area within bounding box 972 (e.g., all of bounding box 972).

In some examples, assignment module 208 may determine an amount of overlap of one or more teeth and a vertical mesial edge of the bounding box, and assign the attachment to the tooth of the one or more teeth with the greatest amount of overlap. In FIG. 9C, a vertical mesial edge of bounding box 972 may overlap tooth 962.

In some examples, the assignment of the attachment to the tooth may be constrained to assignment to teeth likely to be in a photo based on a particular view from which the photo is taken. For example, in FIG. 9C, a rightmost bounding box visible may be less reliably identified and/or assigned based on the view such that assignment module 208 may not perform this assignment, but may perform assignment for attachment 970 and tooth 962. In an anterior view, the teeth likely to be in the photo may be the central and lateral incisors and the canines. In a left lateral view, the teeth likely to be in the photo may be the central incisors, left lateral incisors, the left canines, the first and second left bicuspids, and the first left molars. In a right lateral view, the teeth likely to be in the photo may be the central incisors, right lateral incisors, the right canines, the first and second right bicuspids, and the first right molars.

Although FIGS. 9A and 9C generally depict up to a single attachment on each tooth, in other examples, a tooth may include 0, 1, 2 or another number of attachments. Assignment module 208 may determine the number of attachments that should be on each tooth based on the number of attachments placed on each tooth in the patient's treatment plan (e.g., patient data 228).

Turning back to FIG. 8, at step 810 one or more of the systems described herein may combine the assignments of each of the plurality of images for attachment detection results. For example, assignment module 208 may combine the assignments for each image of image data 222 and combine the assignments, the results of which may be stored in attachment data 234.

The systems described herein may perform step 810 in a variety of ways. In one example, combining the assignments of each of the plurality of images for attachment detection results may include, for each image, identifying which teeth can be seen in the image, and determining for each respective tooth, whether or not a single image of the plurality of images depicts the expected number of attachments on the respective tooth.

In some examples, assignment module 208 may determine that an attachment is missing if a single image depicts less than the expected number of attachments. In some examples, assignment module 208 may determine that an attachment is missing if the plurality of images depicts less than the expected number of attachments.

In some examples, assignment module 208 may, for each image, identify which teeth can be seen in the image, and determine that an attachment is missing when less than a majority of the plurality of images that depict the tooth also depict the expected number of attachments.

In some examples, assignment module 208 may, for each image, identify which teeth can be seen in the image, and determine that an attachment is missing when a majority of the plurality of images that depict the tooth also depict less than then expected number of attachments.

Although method 800 is presented as a sequence of steps, in some examples, the steps of method 800 may be repeated as needed to provide continuous feedback, improve assessment, and/or track changes over time. Thus, certain steps may be repeated, and data may be continuously updated.

Although the examples herein are described with respect to orthodontic care, in other implementations the remote care may include any other medical care that may be conducted via external photography.

Computing System

Figure 10:
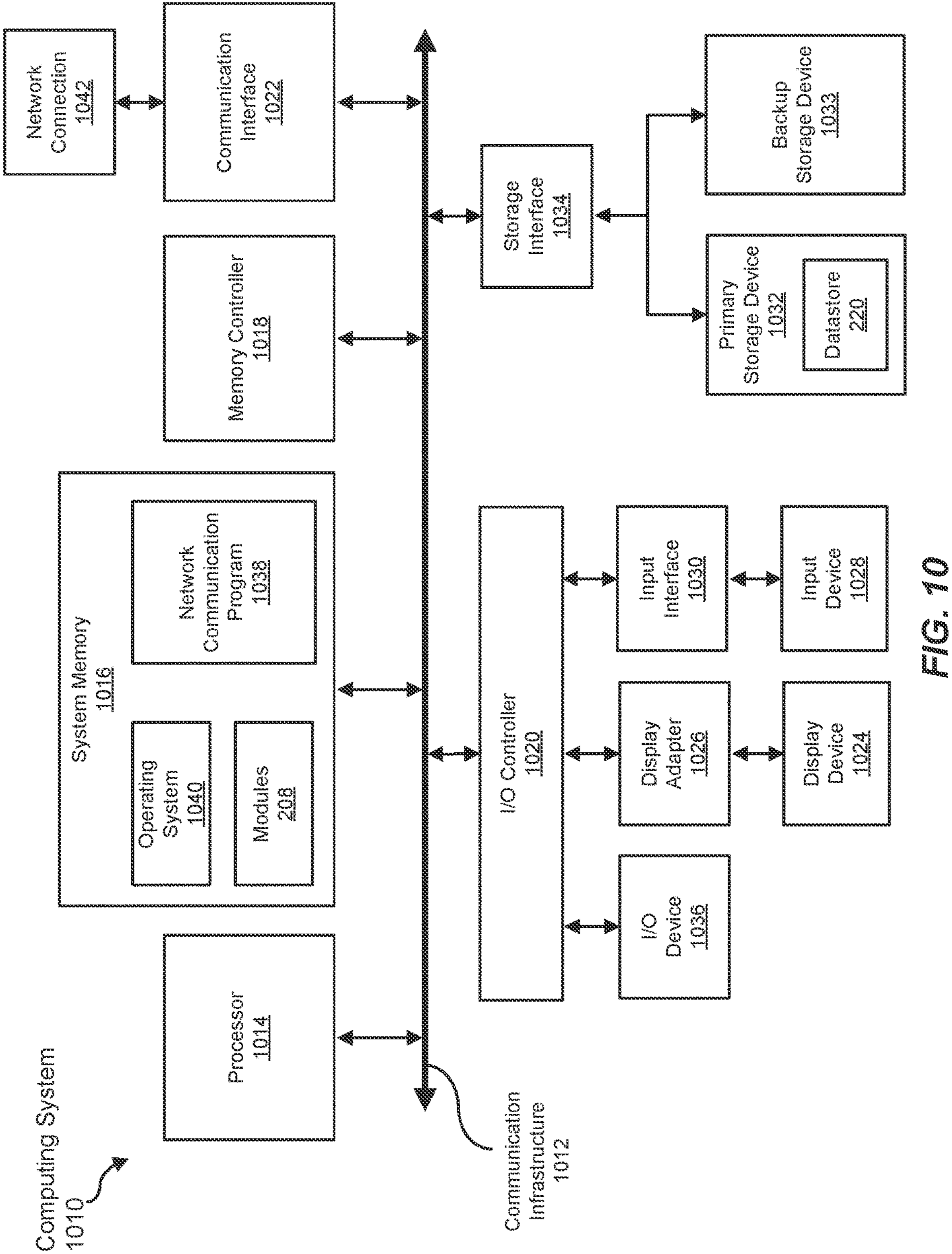
FIG. 10 shows a block diagram of an example computing system capable of implementing one or more embodiments described and/or illustrated herein, in accordance with some embodiments.

FIG. 10 is a block diagram of an example computing system 1010 capable of implementing one or more of the embodiments described and/or illustrated herein. For example, all or a portion of computing system 1010 may perform and/or be a means for performing, either alone or in combination with other elements, one or more of the steps described herein (such as one or more of the steps illustrated in FIGS. 1B-1E, 5, and 8). All or a portion of computing system 1010 may also perform and/or be a means for performing any other steps, methods, or processes described and/or illustrated herein.

Computing system 1010 broadly represents any single or multi-processor computing device or system capable of executing computer-readable instructions. Examples of computing system 1010 include, without limitation, workstations, laptops, client-side terminals, servers, distributed computing systems, handheld devices, or any other computing system or device. In its most basic configuration, computing system 1010 may include at least one processor 1014 and a system memory 1016.

Processor 1014 generally represents any type or form of physical processing unit (e.g., a hardware-implemented central processing unit) capable of processing data or interpreting and executing instructions. In certain embodiments, processor 1014 may receive instructions from a software application or module. These instructions may cause processor 1014 to perform the functions of one or more of the example embodiments described and/or illustrated herein.

System memory 1016 generally represents any type or form of volatile or non-volatile storage device or medium capable of storing data and/or other computer-readable instructions. Examples of system memory 1016 include, without limitation, Random Access Memory (RAM), Read Only Memory (ROM), flash memory, or any other suitable memory device. Although not required, in certain embodiments computing system 1010 may include both a volatile memory unit (such as, for example, system memory 1016) and a non-volatile storage device (such as, for example, primary storage device 1032, as described in detail below). In one example, one or more of virtual dental care modules 108 from FIG. 1A may be loaded into system memory 1016.

In some examples, system memory 1016 may store and/or load an operating system 1040 for execution by processor 1014. In one example, operating system 1040 may include and/or represent software that manages computer hardware and software resources and/or provides common services to computer programs and/or applications on computing system 1010. Examples of operating system 1040 include, without limitation, LINUX, JUNOS, MICROSOFT WINDOWS, WINDOWS MOBILE, MAC OS, APPLE'S IOS, UNIX, GOOGLE CHROME OS, GOOGLE'S ANDROID, SOLARIS, variations of one or more of the same, and/or any other suitable operating system.

In certain embodiments, example computing system 1010 may also include one or more components or elements in addition to processor 1014 and system memory 1016. For example, as illustrated in FIG. 10, computing system 1010 may include a memory controller 1018, an Input/Output (I/O) controller 1020, and a communication interface 1022, each of which may be interconnected via a communication infrastructure 1012. Communication infrastructure 1012 generally represents any type or form of infrastructure capable of facilitating communication between one or more components of a computing device. Examples of communication infrastructure 1012 include, without limitation, a communication bus (such as an Industry Standard Architecture (ISA), Peripheral Component Interconnect (PCI), PCI Express (PCIe), or similar bus) and a network.

Memory controller 1018 generally represents any type or form of device capable of handling memory or data or controlling communication between one or more components of computing system 1010. For example, in certain embodiments memory controller 1018 may control communication between processor 1014, system memory 1016, and I/O controller 1020 via communication infrastructure 1012.

I/O controller 1020 generally represents any type or form of module capable of coordinating and/or controlling the input and output functions of a computing device. For example, in certain embodiments I/O controller 1020 may control or facilitate transfer of data between one or more elements of computing system 1010, such as processor 1014, system memory 1016, communication interface 1022, display adapter 1026, input interface 1030, and storage interface 1034.

As illustrated in FIG. 10, computing system 1010 may also include at least one display device 1024 coupled to I/O controller 1020 via a display adapter 1026. Display device 1024 generally represents any type or form of device capable of visually displaying information forwarded by display adapter 1026. Similarly, display adapter 1026 generally represents any type or form of device configured to forward graphics, text, and other data from communication infrastructure 1012 (or from a frame buffer, as known in the art) for display on display device 1024.

As illustrated in FIG. 10, example computing system 1010 may also include at least one input device 1028 coupled to I/O controller 1020 via an input interface 1030. Input device 1028 generally represents any type or form of input device capable of providing input, either computer or human generated, to example computing system 1010. Examples of input device 1028 include, without limitation, a keyboard, a pointing device, a speech recognition device, variations or combinations of one or more of the same, and/or any other input device.

Additionally or alternatively, example computing system 1010 may include additional I/O devices. For example, example computing system 1010 may include I/O device 1036. In this example, I/O device 1036 may include and/or represent a user interface that facilitates human interaction with computing system 1010. Examples of I/O device 1036 include, without limitation, a computer mouse, a keyboard, a monitor, a printer, a modem, a camera, a scanner, a microphone, a touchscreen device, variations or combinations of one or more of the same, and/or any other I/O device.

Communication interface 1022 broadly represents any type or form of communication device or adapter capable of facilitating communication between example computing system 1010 and one or more additional devices. For example, in certain embodiments communication interface 1022 may facilitate communication between computing system 1010 and a private or public network including additional computing systems. Examples of communication interface 1022 include, without limitation, a wired network interface (such as a network interface card), a wireless network interface (such as a wireless network interface card), a modem, and any other suitable interface. In at least one embodiment, communication interface 1022 may provide a direct connection to a remote server via a direct link to a network, such as the Internet. Communication interface 1022 may also indirectly provide such a connection through, for example, a local area network (such as an Ethernet network), a personal area network, a telephone or cable network, a cellular telephone connection, a satellite data connection, or any other suitable connection.

In certain embodiments, communication interface 1022 may also represent a host adapter configured to facilitate communication between computing system 1010 and one or more additional network or storage devices via an external bus or communications channel. Examples of host adapters include, without limitation, Small Computer System Interface (SCSI) host adapters, Universal Serial Bus (USB) host adapters, Institute of Electrical and Electronics Engineers (IEEE) 1394 host adapters, Advanced Technology Attachment (ATA), Parallel ATA (PATA), Serial ATA (SATA), and External SATA (eSATA) host adapters, Fibre Channel interface adapters, Ethernet adapters, or the like. Communication interface 1022 may also allow computing system 1010 to engage in distributed or remote computing. For example, communication interface 1022 may receive instructions from a remote device or send instructions to a remote device for execution.

In some examples, system memory 1016 may store and/or load a network communication program 1038 for execution by processor 1014. In one example, network communication program 1038 may include and/or represent software that enables computing system 1010 to establish a network connection 1042 with another computing system (not illustrated in FIG. 10) and/or communicate with the other computing system by way of communication interface 1022. In this example, network communication program 1038 may direct the flow of outgoing traffic that is sent to the other computing system via network connection 1042. Additionally or alternatively, network communication program 1038 may direct the processing of incoming traffic that is received from the other computing system via network connection 1042 in connection with processor 1014.

Although not illustrated in this way in FIG. 10, network communication program 1038 may alternatively be stored and/or loaded in communication interface 1022. For example, network communication program 1038 may include and/or represent at least a portion of software and/or firmware that is executed by a processor and/or Application Specific Integrated Circuit (ASIC) incorporated in communication interface 1022.

As illustrated in FIG. 10, example computing system 1010 may also include a primary storage device 1032 and a backup storage device 1033 coupled to communication infrastructure 1012 via a storage interface 1034. Storage devices 1032 and 1033 generally represent any type or form of storage device or medium capable of storing data and/or other computer-readable instructions. For example, storage devices 1032 and 1033 may be a magnetic disk drive (e.g., a so-called hard drive), a solid state drive, a floppy disk drive, a magnetic tape drive, an optical disk drive, a flash drive, or the like. Storage interface 1034 generally represents any type or form of interface or device for transferring data between storage devices 1032 and 1033 and other components of computing system 1010. In one example, virtual dental care datastore(s) 120 from FIG. 1A may be stored and/or loaded in primary storage device 1032.

In certain embodiments, storage devices 1032 and 1033 may be configured to read from and/or write to a removable storage unit configured to store computer software, data, or other computer-readable information. Examples of suitable removable storage units include, without limitation, a floppy disk, a magnetic tape, an optical disk, a flash memory device, or the like. Storage devices 1032 and 1033 may also include other similar structures or devices for allowing computer software, data, or other computer-readable instructions to be loaded into computing system 1010. For example, storage devices 1032 and 1033 may be configured to read and write software, data, or other computer-readable information. Storage devices 1032 and 1033 may also be a part of computing system 1010 or may be a separate device accessed through other interface systems.

Many other devices or subsystems may be connected to computing system 1010. Conversely, all of the components and devices illustrated in FIG. 10 need not be present to practice the embodiments described and/or illustrated herein. The devices and subsystems referenced above may also be interconnected in different ways from that shown in FIG. 10. Computing system 1010 may also employ any number of software, firmware, and/or hardware configurations. For example, one or more of the example embodiments disclosed herein may be encoded as a computer program (also referred to as computer software, software applications, computer-readable instructions, or computer control logic) on a computer-readable medium. The term "computer-readable medium," as used herein, generally refers to any form of device, carrier, or medium capable of storing or carrying computer-readable instructions. Examples of computer-readable media include, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

The computer-readable medium containing the computer program may be loaded into computing system 1010. All or a portion of the computer program stored on the computer-readable medium may then be stored in system memory 1016 and/or various portions of storage devices 1032 and 1033. When executed by processor 1014, a computer program loaded into computing system 1010 may cause processor 1014 to perform and/or be a means for performing the functions of one or more of the example embodiments described and/or illustrated herein. Additionally or alternatively, one or more of the example embodiments described and/or illustrated herein may be implemented in firmware and/or hardware. For example, computing system 1010 may be configured as an Application Specific Integrated Circuit (ASIC) adapted to implement one or more of the example embodiments disclosed herein.

Figure 11:
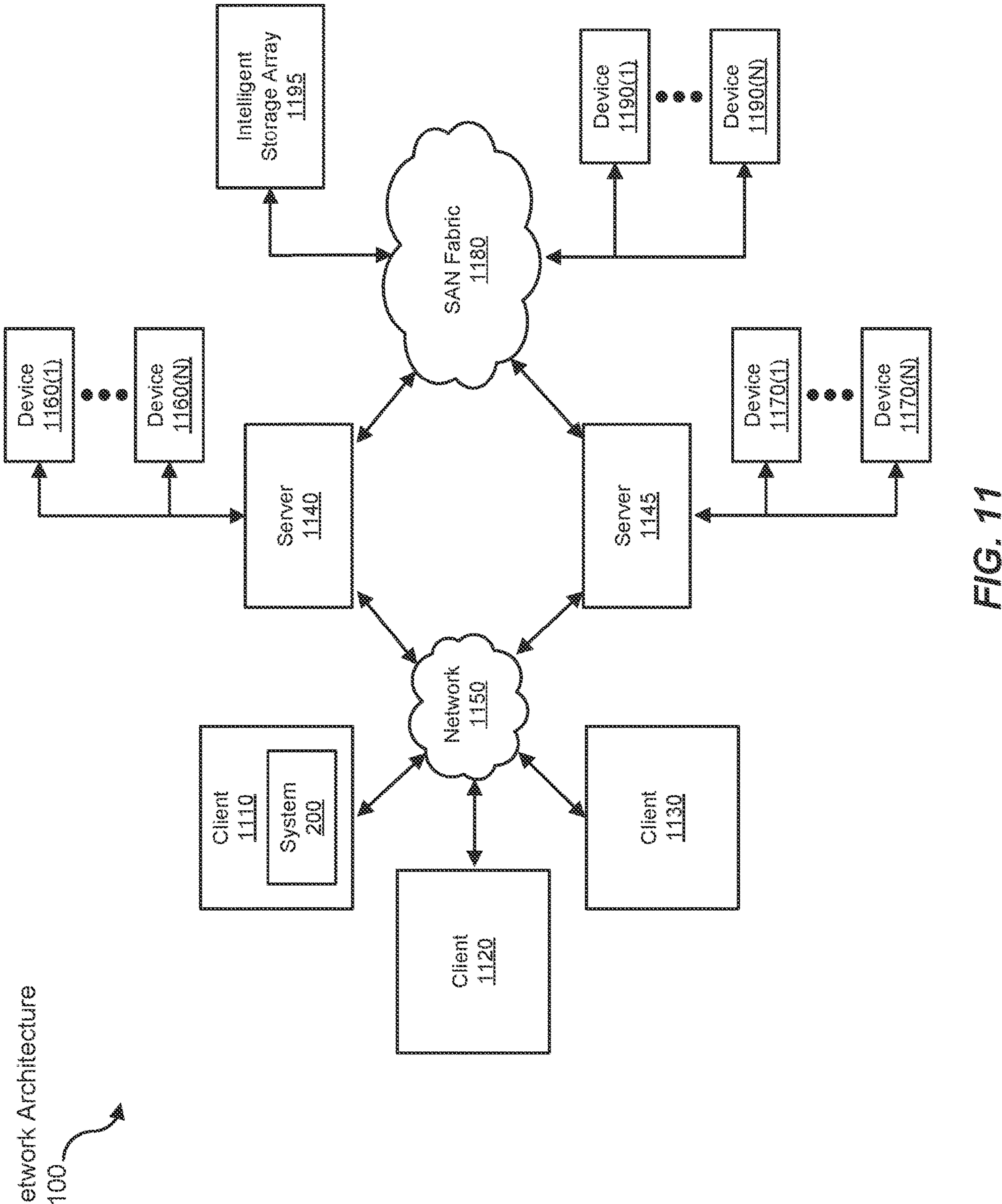
FIG. 11 shows a block diagram of an example computing network capable of implementing one or more of the embodiments described and/or illustrated herein, in accordance with some embodiments.

FIG. 11 is a block diagram of an example network architecture 1100 in which client systems 1110, 1120, and 1130 and servers 1140 and 1145 may be coupled to a network 1150. As detailed above, all or a portion of network architecture 1100 may perform and/or be a means for performing, either alone or in combination with other elements, one or more of the steps disclosed herein (such as one or more of the steps illustrated in FIGS. 1B-1E, 5, and 8). All or a portion of network architecture 1100 may also be used to perform and/or be a means for performing other steps and features set forth in the instant disclosure.

Client systems 1110, 1120, and 1130 generally represent any type or form of computing device or system, such as example computing system 1010 in FIG. 10. Similarly, servers 1140 and 1145 generally represent computing devices or systems, such as application servers or database servers, configured to provide various database services and/or run certain software applications. Network 1150 generally represents any telecommunication or computer network including, for example, an intranet, a WAN, a LAN, a PAN, or the Internet. In one example, client systems 1110, 1120, and/or 1130 and/or servers 1140 and/or 1145 may include all or a portion of system 100 from FIG. 1A.

As illustrated in FIG. 11, one or more storage devices 1160(1)-(N) may be directly attached to server 1140. Similarly, one or more storage devices 1170(1)-(N) may be directly attached to server 1145. Storage devices 1160(1)-(N) and storage devices 1170(1)-(N) generally represent any type or form of storage device or medium capable of storing data and/or other computer-readable instructions. In certain embodiments, storage devices 1160(1)-(N) and storage devices 1170(1)-(N) may represent Network-Attached Storage (NAS) devices configured to communicate with servers 1140 and 1145 using various protocols, such as Network File System (NFS), Server Message Block (SMB), or Common Internet File System (CIFS).

Servers 1140 and 1145 may also be connected to a Storage Area Network (SAN) fabric 1180. SAN fabric 1180 generally represents any type or form of computer network or architecture capable of facilitating communication between a plurality of storage devices. SAN fabric 1180 may facilitate communication between servers 1140 and 1145 and a plurality of storage devices 1190(1)-(N) and/or an intelligent storage array 1195. SAN fabric 1180 may also facilitate, via network 1150 and servers 1140 and 1145, communication between client systems 1110, 1120, and 1130 and storage devices 1190(1)-(N) and/or intelligent storage array 1195 in such a manner that devices 1190(1)-(N) and array 1195 appear as locally attached devices to client systems 1110, 1120, and 1130. As with storage devices 1160(1)-(N) and storage devices 1170(1)-(N), storage devices 1190(1)-(N) and intelligent storage array 1195 generally represent any type or form of storage device or medium capable of storing data and/or other computer-readable instructions.

In certain embodiments, and with reference to example computing system 1010 of FIG. 10, a communication interface, such as communication interface 1022 in FIG. 10, may be used to provide connectivity between each client system 1110, 1120, and 1130 and network 1150. Client systems 1110, 1120, and 1130 may be able to access information on server 1140 or 1145 using, for example, a web browser or other client software. Such software may allow client systems 1110, 1120, and 1130 to access data hosted by server 1140, server 1145, storage devices 1160(1)-(N), storage devices 1170(1)-(N), storage devices 1190(1)-(N), or intelligent storage array 1195. Although FIG. 11 depicts the use of a network (such as the Internet) for exchanging data, the embodiments described and/or illustrated herein are not limited to the Internet or any particular network-based environment.

In at least one embodiment, all or a portion of one or more of the example embodiments disclosed herein may be encoded as a computer program and loaded onto and executed by server 1140, server 1145, storage devices 1160 (1)-(N), storage devices 1170(1)-(N), storage devices 1190 (1)-(N), intelligent storage array 1195, or any combination thereof. All or a portion of one or more of the example embodiments disclosed herein may also be encoded as a computer program, stored in server 1140, run by server 1145, and distributed to client systems 1110, 1120, and 1130 over network 1150.

As detailed above, computing system 1010 and/or one or more components of network architecture 1100 may perform and/or be a means for performing, either alone or in combination with other elements, one or more steps of an example method for virtual care.

The virtual care system described herein may allow the patient's doctor to remotely monitor aspects of the patient's treatment progression. Such monitoring may allow early intervention when needed. For example, in response to the notification, the doctor may recommend certain actions or changes in treatment, such as repeating a particular stage, using chewable object (e.g., "chewies") to help the patient chew the orthodontic appliance into place, restart treatment, etc.

While the foregoing disclosure sets forth various embodiments using specific block diagrams, flowcharts, and examples, each block diagram component, flowchart step, operation, and/or component described and/or illustrated herein may be implemented, individually and/or collectively, using a wide range of hardware, software, or firmware (or any combination thereof) configurations. In addition, any disclosure of components contained within other components should be considered example in nature since many other architectures can be implemented to achieve the same functionality.

In some examples, all or a portion of example system 100 in FIG. 1A may represent portions of a cloud-computing or network-based environment. Cloud-computing environments may provide various services and applications via the Internet. These cloud-based services (e.g., software as a service, platform as a service, infrastructure as a service, etc.) may be accessible through a web browser or other remote interface. Various functions described herein may be provided through a remote desktop environment or any other cloud-based computing environment.

In various embodiments, all or a portion of example system 100 in FIG. 1A may facilitate multi-tenancy within a cloud-based computing environment. In other words, the software modules described herein may configure a computing system (e.g., a server) to facilitate multi-tenancy for one or more of the functions described herein. For example, one or more of the software modules described herein may program a server to enable two or more clients (e.g., customers) to share an application that is running on the server. A server programmed in this manner may share an application, operating system, processing system, and/or storage system among multiple customers (i.e., tenants). One or more of the modules described herein may also partition data and/or configuration information of a multi-tenant application for each customer such that one customer cannot access data and/or configuration information of another customer.

According to various embodiments, all or a portion of example system 100 in FIG. 1A may be implemented within a virtual environment. For example, the modules and/or data described herein may reside and/or execute within a virtual machine. As used herein, the term "virtual machine" generally refers to any operating system environment that is abstracted from computing hardware by a virtual machine manager (e.g., a hypervisor). Additionally or alternatively, the modules and/or data described herein may reside and/or execute within a virtualization layer. As used herein, the term "virtualization layer" generally refers to any data layer and/or application layer that overlays and/or is abstracted from an operating system environment. A virtualization layer may be managed by a software virtualization solution (e.g., a file system filter) that presents the virtualization layer as though it were part of an underlying base operating system. For example, a software virtualization solution may redirect calls that are initially directed to locations within a base file system and/or registry to locations within a virtualization layer.

In some examples, all or a portion of example system 100 in FIG. 1A may represent portions of a mobile computing environment. Mobile computing environments may be implemented by a wide range of mobile computing devices, including mobile phones, tablet computers, e-book readers, personal digital assistants, wearable computing devices (e.g., computing devices with a head-mounted display, smartwatches, etc.), and the like. In some examples, mobile computing environments may have one or more distinct features, including, for example, reliance on battery power, presenting only one foreground application at any given time, remote management features, touchscreen features, location and movement data (e.g., provided by Global Positioning Systems, gyroscopes, accelerometers, etc.), restricted platforms that restrict modifications to system-level configurations and/or that limit the ability of third-party software to inspect the behavior of other applications, controls to restrict the installation of applications (e.g., to only originate from approved application stores), etc. Various functions described herein may be provided for a mobile computing environment and/or may interact with a mobile computing environment.

In addition, all or a portion of example system 100 in FIG. 1A may represent portions of, interact with, consume data produced by, and/or produce data consumed by one or more systems for information management. As used herein, the term "information management" may refer to the protection, organization, and/or storage of data. Examples of systems for information management may include, without limitation, storage systems, backup systems, archival systems, replication systems, high availability systems, data search systems, virtualization systems, and the like.

In some embodiments, all or a portion of example system 100 in FIG. 1A may represent portions of, produce data protected by, and/or communicate with one or more systems for information security. As used herein, the term "information security" may refer to the control of access to protected data. Examples of systems for information security may include, without limitation, systems providing managed security services, data loss prevention systems, identity authentication systems, access control systems, encryption systems, policy compliance systems, intrusion detection and prevention systems, electronic discovery systems, and the like.

The process parameters and sequence of steps described and/or illustrated herein are given by way of example only and can be varied as desired. For example, while the steps illustrated and/or described herein may be shown or discussed in a particular order, these steps do not necessarily need to be performed in the order illustrated or discussed. The various example methods described and/or illustrated herein may also omit one or more of the steps described or illustrated herein or include additional steps in addition to those disclosed.

While various embodiments have been described and/or illustrated herein in the context of fully functional computing systems, one or more of these example embodiments may be distributed as a program product in a variety of forms, regardless of the particular type of computer-readable media used to actually carry out the distribution. The embodiments disclosed herein may also be implemented using software modules that perform certain tasks. These software modules may include script, batch, or other executable files that may be stored on a computer-readable storage medium or in a computing system. In some embodiments, these software modules may configure a computing system to perform one or more of the example embodiments disclosed herein.

As described herein, the computing devices and systems described and/or illustrated herein broadly represent any type or form of computing device or system capable of executing computer-readable instructions, such as those contained within the modules described herein. In their most basic configuration, these computing device(s) may each comprise at least one memory device and at least one physical processor.

The term "memory" or "memory device," as used herein, generally represents any type or form of volatile or non-volatile storage device or medium capable of storing data and/or computer-readable instructions. In one example, a memory device may store, load, and/or maintain one or more of the modules described herein. Examples of memory devices comprise, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In addition, the term "processor" or "physical processor," as used herein, generally refers to any type or form of hardware-implemented processing unit capable of interpreting and/or executing computer-readable instructions. In one example, a physical processor may access and/or modify one or more modules stored in the above-described memory device. Examples of physical processors comprise, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor.

Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step.

In addition, one or more of the devices described herein may transform data, physical devices, and/or representations of physical devices from one form to another. Additionally or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

The term "computer-readable medium," as used herein, generally refers to any form of device, carrier, or medium capable of storing or carrying computer-readable instructions. Examples of computer-readable media comprise, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

The processor as described herein can be configured to perform one or more steps of any method disclosed herein. Alternatively or in combination, the processor can be configured to combine one or more steps of one or more methods as disclosed herein.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of" Finally, for ease of use, the terms "including" and "having" (and their derivatives), as used in the specification and claims, are interchangeable with and shall have the same meaning as the word "comprising.

The processor as disclosed herein can be configured with instructions to perform any one or more steps of any method as disclosed herein.

It will be understood that although the terms "first," "second," "third", etc. may be used herein to describe various layers, elements, components, regions or sections without referring to any particular order or sequence of events. These terms are merely used to distinguish one layer, element, component, region or section from another layer, element, component, region or section. A first layer, element, component, region or section as described herein could be referred to as a second layer, element, component, region or section without departing from the teachings of the present disclosure.

As used herein, the term "or" is used inclusively to refer items in the alternative and in combination.

As used herein, characters such as numerals refer to like elements. The present disclosure includes the following numbered clauses.

Clause 1. A method for dental treatment comprising: receiving a plurality of images of a patient, the plurality of images including the patient's dentition and an orthodontic appliance, while the patient is wearing the orthodontic appliance; determining whether each of the plurality of images satisfy a plurality of detection criteria, the plurality of detection criteria including criteria for image quality and detection criteria for clinical acceptability of the image of the patient's dentition; segmenting the teeth in the images to individually identify each tooth in the image; segmenting the images using a threshold-based segmentation to classify pixel of the image as being of the orthodontic appliance or the teeth; classifying the pixels of the image as being pixels belonging to a space between an aligner and a tooth; assigning the pixels belonging to a space to one or more of the individual teeth; determining a conversion between image-based spatial measurements to real-world spatial measurements by projecting a tooth from the treatment plan into a plane that corresponds to a plane of a corresponding tooth in the image; and determining, from the plurality of images using the conversion, a size of each of the one or more spaces.

Clause 2. The method of clause 1, wherein segmenting the image may include edge based segmentation.

Clause 3. The method of clause 1, wherein determining a conversion metric between image-based spatial measurements to real-world spatial measurements includes: determining a conversion from image size to real-world size based on a relationship between a real-world size of the patient's teeth from a patient's treatment plan and an image size of the patient's teeth in the image.

Clause 4. The method of clause 3, wherein the real-world size of the patient's teeth from a patient's treatment plan is from a three-dimensional model of the patient's teeth.

Clause 5. The method of clause 3, wherein the conversion is a pixel dimension.

Clause 6. The method of clause 3, wherein the conversion is a pixel's length and width.

Clause 7. The method of clause 3, wherein the relationship is a relationship between a width of the teeth, a length of the facial-axis of a clinical crown (FACC), or an overall tooth area, of each of a set of the patient's teeth in the treatment plan and each corresponding teeth in the image.

Clause 8. The method of clause 1, wherein the images include a two-dimensional digital photo.

Clause 9. The method of clause 1, wherein the criteria for image quality includes criteria for image exposure.

Clause 10. The method of clause 9, wherein the criteria for image exposure includes criteria for determining that the image is bright enough to distinguish the teeth and the appliance.

Clause 11. The method of clause 9, wherein the criteria for image exposure includes criteria for determining that the image is not so dark that the teeth and the appliance are not distinguishable from each other.

Clause 12. The method of clause 9, wherein the criteria for image exposure includes criteria for image sharpness or image blurriness.

Clause 13. The method of clause 12, wherein the criteria for image sharpness or image blurriness includes criteria for determining that the image is sufficiently sharp to distinguish the teeth and the appliance.

Clause 14. The method of clause 12, wherein the criteria for image sharpness or image blurriness includes criteria for determining that the image is not so blurry that the teeth and the appliance are not distinguishable from each other.

Clause 15. The method of clause 1, wherein the criteria for image quality includes criteria for image contrast.

Clause 16. The method of clause 15, wherein the criteria for image contrast includes criteria for determining that the image has sufficient contrast to distinguish the teeth and the appliance.

Clause 17. The method of clause 15, wherein the criteria for image contrast includes criteria for determining that the contrast is not so low that the teeth and the appliance are not distinguishable from each other.

Clause 18. The method of clause 1, wherein the detection criteria for clinical acceptability of the image of the patient's dentition includes criteria for determining whether or not cheek retractors were used during the image capture process.

Clause 19. The method of clause 18, further comprising, determining if cheek retractors are present in the image.

Clause 20. The method of clause 18, further comprising, determining whether or not cheek retractors were used during the image capture process based on lip shape.

Clause 21. The method of clause 1, wherein the detection criteria for clinical acceptability of the image of the patient's dentition includes determining whether posterior teeth of the patient's dentition are present in the image.

Clause 22. The method of clause 1, wherein the detection criteria for clinical acceptability of the image of the patient's dentition includes a criteria for determining the patient's bite is open in the image.

Clause 23. The method of clause 22, wherein the detection criteria for clinical acceptability of the image of the patient's dentition includes a criteria for determining the patient's bite is open sufficiently that teeth of an upper arch are not in contact with teeth of a lower arch.

Clause 24. The method of clause 1, wherein the detection criteria for clinical acceptability of the image of the patient's dentition includes a criteria for determining the patient's bite is sufficiently open that the appliance spaces on an upper and lower jaw are distinguishable in the image.

Clause 25. The method of clause 1 further comprising: selecting a subset of the images that fail one or more detection criteria; providing an indication to a dental professional that the subset of images fail one or more detection criteria; and receiving a clinical assessment of appliance fit from the dental professional based on the subset of images.

Clause 26. The method of clause 7, wherein the set of teeth are incisors.

Clause 27. The method of clause 7, further comprising projecting a tooth from the treatment plan into a plane that corresponds to a plane of a corresponding tooth in the image.

Clause The method of clause 1, further comprising subtracting the identified appliance space from the identified teeth in the images.

Clause 29. The method of clause 1, further comprising assigning each pixel identified as appliance space to a tooth.

Clause 30. The method of clause 29, wherein assigning each pixel identified as appliance space to a tooth includes: determining a boundary for a tooth between each adjacent tooth; extending the boundary beyond an end of the tooth as a boundary line; and assigning the appliance space between the boundary lines to the corresponding tooth.

Clause 31. The method of clause 30, wherein determining the size of each space comprises: identifying a vertical orientation of teeth in each of the plurality of images; measuring a largest number of pixels of appliance space in the vertical orientation between respective boundary lines; and converting, for each space using the conversion metric, the largest number of pixels into a real-world spatial size.

Clause 32. The method of clause 29, wherein assigning each pixel identified as appliance space to a tooth includes: using a distance transform for each pixel to find a distance of each pixel to the nearest tooth; and assigning the pixel to the nearest tooth.

Clause 33. The method of clause 32, wherein the size of each of the appliance space for each tooth is determined based on a largest distance between an appliance space pixel and the respective tooth.

Clause 34. The method of clause 1, further comprising: receiving a second plurality of images of the patient; determining, from the second plurality of images, a second size of each of the one or more spaces; and determining that the appliance space is increasing or decreasing over time based on the size and the second size.

Clause 35. The method of clause 1, wherein: identifying one or more spaces further includes: determining, in a treatment plan, an planned space; locating pixels identified as spaces in the image that correspond to the planned space form the treatment plan; and changing the identification of the pixels to something other than a space.

Clause 36. The method of clause 35, wherein changing the identification of the pixels to something other than a space includes changing the identification to a planned space.

Clause 37. The method of clause 35, wherein determining, from the plurality of images using the conversion metric, a size of each of the one or more spaces does not include the planned space.

Clause 38. The method of clause 35, wherein the planned space is a space to accommodate orthodontic movement of a tooth.

Clause 39. The method of clause 35, wherein the planned space is a space to accommodate eruption of a tooth.

Clause 40. A system comprising: a processor; and memory including instructions to carry out the method of any of clauses 1-40.

Clause 41. A method for dental treatment comprising: receiving a plurality of images of a patient's dentition; identifying, from the plurality of images, individual teeth of the patient's dentition; detecting, from the plurality of images, one or more attachments on the patient's dentition; assigning, based on each of the plurality of images, each of the one or more attachments to one of the individual teeth in each image; and combining the assignments of each of the plurality of images for attachment detection results.

Clause 42. The method of clause 41, wherein identifying, from the plurality of images, individual teeth of the patient's dentition includes segmenting the individual teeth of the patient's dentition contained in the image.

Clause 43. The method of clause 42, wherein segmenting the individual teeth includes determining which teeth are located in the image and which pixels of the image are a part of each tooth.

Clause 44. The method of clause 41, wherein the identifying the individual teeth includes assigning each identified tooth to a corresponding tooth in a patient's treatment plan.

Clause 45. The method of clause 44, wherein the identifying the individual teeth includes removing a tooth that is not present in the patient's treatment plan.

Clause 46. The method of clause 41, further comprising: forming a bounding box around each detected attachment.

Clause 47. The method of clause 46, wherein assigning each of the one or more attachments to one of the individual teeth includes: determining a center point of the attachment bounding box; and assigning the attachment to a tooth of the individual teeth based on where the center point is located.

Clause 48. The method of clause 46, wherein assigning each of the one or more attachments to one of the individual teeth includes: determining a center point of the attachment bounding box; and assigning the attachment to a tooth of the individual teeth based on a nearest tooth to where the center point is located.

Clause 49. The method of clause 46, wherein assigning each of the one or more attachments to one of the individual teeth includes: determining an area of each tooth within the bounding box; and assigning the attachment to the tooth based on which tooth has a greatest area within the bounding box.

Clause 50. The method of clause 46, wherein assigning each of the one or more attachments to one of the individual teeth includes: determining an amount of overlap of one or more teeth and a vertical mesial edge of the bounding box; and assigning the attachment to a tooth of the one or more teeth with the greatest amount of overlap.

Clause 51. The method of any one of clauses 47-49 wherein assigning the attachment to the tooth is constrained to teeth likely to be in a photo based on a particular view from which the photo is taken.

Clause 52. The method of clause 51, wherein in an anterior view the teeth likely to be in the photo are central and lateral incisors and canines.

Clause 53. The method of clause 51, wherein in a left lateral view the teeth likely to be in the photo are central incisors, left lateral incisors, left canines, first and second left bicuspids, and first left molars.

Clause 54. The method of clause 51, wherein in a right lateral view the teeth likely to be in the photo are central incisors, right lateral incisors, right canines, first and second right bicuspids, and first right molars.

Clause 55. The method of clause 41, further comprising: determining a number of attachments that should be on each tooth based on the number of attachments placed on each tooth in the patient's treatment plan.

Clause 56. The method of clause 41, wherein combining the assignments of each of the plurality of images for attachment detection results includes: for each image, identifying which teeth can be seen in the image; and determining for each respective tooth, whether or not a single image of the plurality of images depicts an expected number of attachments on the respective tooth.

Clause 57. The method of clause 56, further comprising: determining that an attachment is missing if a single image depicts less than the expected number of attachments.

Clause 58. The method of clause 56, further comprising: determining that an attachment is missing if the plurality of images depicts less than the expected number of attachments.

Clause 59. The method of clause 41, wherein combining the assignments of each of the plurality of images for attachment detection results includes: for each image, identifying which teeth can be seen in the image; and determining that an attachment is missing when less than a majority of the plurality of images that depict the tooth also depict an expected number of attachments.

Clause 60. The method of clause 41, wherein combining the assignments of each of the plurality of images for attachment detection results includes: for each image, identifying which teeth can be seen in the image; and determining that an attachment is missing when a majority of the plurality of images that depict the tooth also depict less than an expected number of attachments.

Clause 61. The method of clause 41, wherein the plurality of images include images with arches in an open-bite.

Clause 62. The method of clause 41, wherein the plurality of images include images with arches in a closed-bite.

Clause 63. The method of clause 41, wherein the plurality of images include an anterior image with arches in an open-bite, a left lateral image with the arches in the open-bite, a right lateral image with the arches in the open-bite, an anterior image with the arches in a closed-bite, a left lateral image with the arches in the closed-bite, and a right lateral image with the arches in the closed-bite.

Clause 64. A system comprising: a processor; and memory including instructions to carry out the method of any of clauses 42-63.

Clause 65. A computer-implemented method for digital treatment planning, the computer-implemented method comprising: receiving one or more two-dimensional (2D) images of a dentition of a person; identifying one or more teeth associated with the dentition in the one or more 2D images; identifying one or more aligners in the one or more 2D images; analyzing aligner fit of the one or more aligners on the one or more teeth, wherein analyzing aligner fit comprises: determining whether pixels in the one or more 2D images correspond to the one or more aligners but do not correspond to the one or more teeth; responsive to a determination of whether pixels in the one or more 2D images correspond to the one or more aligners but do not correspond to the one or more teeth, identifying spacing information between identified one or more teeth and identified one or more aligners; providing digital treatment planning information for the one or more teeth using the spacing information.

Clause 66. The computer-implemented method of clause 65, further comprising using one or more detection criteria to evaluate whether the one or more 2D images are suitable for analyzing the aligner fit.

Clause 67. The computer-implemented method of clause 66, further comprising analyzing the aligner fit only if the one or more detection criteria indicate the one or more 2D images are suitable for analyzing the aligner fit.

Clause 68. The computer-implemented method of clause 66, wherein using one or more detection criteria to evaluate whether the one or more 2D images are suitable for analyzing the aligner fit comprises using a machine-trained classifier to evaluate whether the one or more 2D images are suitable for analyzing the aligner fit.

Clause 69. The computer-implemented method of clause 68, wherein the machine-trained classifier comprises an image classifier trained with at least a plurality of images of aligners on dentition.

Clause 70. The computer-implemented method of clause 66, wherein the one or more detection criteria comprise clinical acceptability criteria related to the one or more 2D images.

Clause 71. The computer-implemented method of clause 70, wherein the clinical acceptability criteria comprise criteria for evaluating whether the one or more 2D images show a sufficiently open bite in which the dentition is sufficiently open to distinguish first spaces between a first aligner and first teeth on a first jaw and second spaces between a second aligner and second teeth on a second jaw opposite the first jaw.

Clause 72. The computer-implemented method of clause 70, wherein the clinical acceptability criteria comprise criteria for evaluating whether the one or more 2D images show a sufficiently open bite in which the dentition is sufficiently open so that first teeth on a first jaw are not in contact with second teeth on a second jaw opposite the first jaw.

Clause 73. The computer-implemented method of clause 70, wherein the clinical acceptability criteria comprise criteria for evaluating whether or not cheek retractors were used to capture the one or more 2D images.

Clause 74. The computer-implemented method of clause 70, wherein the clinical acceptability criteria comprise criteria for evaluating the absence or presence of cheek retractors in the one or more 2D images.

Clause 75. The computer-implemented method of clause 70, wherein the clinical acceptability criteria comprise criteria for evaluating whether or not a scanning box coupled to a mobile phone was used to capture the one or more 2D images.

Clause 76. The computer-implemented method of clause 66, wherein the one or more detection criteria comprise image quality criteria related to the one or more 2D images.

Clause 77. The computer-implemented method of clause 76, wherein the image quality criteria comprise a measure of brightness or darkness of at least one or more regions of the one or more 2D images.

Clause 78. The computer-implemented method of clause 76, wherein the image quality criteria comprise a measure of sharpness or blurriness of at least one or more regions of the one or more 2D images.

Clause 79. The computer-implemented method of clause 76, wherein the image quality criteria comprise a measure of exposure of at least one or more regions of the one or more 2D images.

Clause 80. The computer-implemented method of clause 76, wherein the image quality criteria comprise a measure of whether or not the one or more aligners are distinguishable from one another in the one or more 2D images.

Clause 81. The computer-implemented method of clause 65, wherein identifying spacing information between identified one or more teeth and identified one or more aligners comprises converting the spacing information on the one or more 2D images to real-world spatial sizes.

Clause 82. The computer-implemented method of clause 81, wherein converting the spacing information to real-world spatial sizes comprises comparing information about one or more teeth from identified one or more teeth on the one or more 2D images with information about a corresponding one or more teeth from a three-dimensional (3D) digital dental model.

Clause 83. The computer-implemented method of clause 65, further comprising segmenting the one or more 2D images into one or more segmented 2D representations comprising individual teeth of the one or more teeth, and the one or more aligners.

Clause 84. The computer-implemented method of clause 83, wherein segmenting the one or more 2D images comprises using a threshold-based segmentation to segment regions of the one or more 2D images into one or more segmented 2D representations comprising individual teeth of the one or more teeth, and the one or more aligners.

Clause 85. The computer-implemented method of clause 83, wherein segmenting the one or more 2D images into one or more segmented 2D representations using a machine-trained classifier to segment regions of the one or more 2D images.

Clause 86. The computer-implemented method of clause 85, wherein the machine-trained classifier comprises a semantic classifier trained to analyze at least a plurality of images of aligners on dentition.

Clause 87. The computer-implemented method of clause 85, wherein the machine-trained classifier comprises an object-based classifier trained to analyze at least a plurality of images of aligners on dentition.

Clause 88. The computer-implemented method of clause 83, further comprising using one or more boundaries between a first plurality of teeth in the one or more segmented 2D representations to identify the spatial information.

Clause 89. The computer-implemented method of clause 88, further comprising identifying the one or more boundaries between the first plurality of teeth.

Clause 90. The computer-implemented method of clause 89, wherein identifying the one or more boundaries between the first plurality of teeth comprises using one or more of a machine-trained classifier and a linear classifier to identify the one or more boundaries between the first plurality of teeth.

Clause 91. The computer-implemented method of clause 88, further comprising: using the one or more boundaries to identify spatial aligner regions of the one or more aligners assigned to each tooth of the first plurality of teeth; using pixels associated with the spatial aligner regions to identify the spacing information.

Clause 92. The computer-implemented method of clause 65, wherein the digital treatment planning information comprises one or more indications indicating whether the one or more aligners appropriately fit the one or more teeth.

Clause 93. The computer-implemented method of clause 65, wherein the digital treatment planning information is displayed on a display of an electronic device.

Clause 94. The computer-implemented method of clause 65, wherein the digital treatment planning information comprises one or more indications indicating whether the digital treatment plan is on track or off track.

Clause 95. The computer-implemented method of clause 65, further comprising directing capture of the one or more 2D images on a mobile phone, a laptop, computing device, or some combination thereof.

Clause 96. A system comprising: one or more processors; memory coupled to the one or more processors, wherein the memory stores computer-program instructions, wherein the computer-program instructions are configured to be executed by the processor to perform a computer-implemented method comprising: receiving one or more two-dimensional (2D) images of a dentition of a person; identifying one or more teeth associated with the dentition in the one or more 2D images; identifying one or more aligners in the one or more 2D images; analyzing aligner fit of the one or more aligners on the one or more teeth, wherein analyzing aligner fit comprises: determining whether pixels in the one or more 2D images correspond to the one or more aligners but do not correspond to the one or more teeth; responsive to a determination of whether pixels in the one or more 2D images correspond to the one or more aligners but do not correspond to the one or more teeth, identifying spacing information between identified one or more teeth and identified one or more aligners; providing digital treatment planning information for the one or more teeth using the spacing information.

Clause 97. A non-transitory computer-readable medium comprising computer-program instructions, wherein the computer-program instructions are configured to execute a computer-implemented method comprising: receiving one or more two-dimensional (2D) images of a dentition of a person; identifying one or more teeth associated with the dentition in the one or more 2D images; identifying one or more aligners in the one or more 2D images; analyzing aligner fit of the one or more aligners on the one or more teeth, wherein analyzing aligner fit comprises: determining whether pixels in the one or more 2D images correspond to the one or more aligners but do not correspond to the one or more teeth; responsive to a determination of whether pixels in the one or more 2D images correspond to the one or more aligners but do not correspond to the one or more teeth, identifying spacing information between identified one or more teeth and identified one or more aligners; providing digital treatment planning information for the one or more teeth using the spacing information.

Embodiments of the present disclosure have been shown and described as set forth herein and are provided by way of example only. One of ordinary skill in the art will recognize numerous adaptations, changes, variations, and substitutions without departing from the scope of the present disclosure. Several alternatives and combinations of the embodiments disclosed herein may be utilized without departing from the scope of the present disclosure and the inventions disclosed herein. Therefore, the scope of the presently disclosed inventions shall be defined solely by the scope of the appended claims and the equivalents thereof.

What is claimed is:

1. A system for dental treatment comprising one or more processors and a memory operably coupled to the one or more processors and storing instructions that, when executed by the one or more processors, cause the system to perform operations comprising:

receiving a plurality of images of a patient's dentition;

identifying, in each of the plurality of images, individual teeth of the patient's dentition;

detecting, in each of the plurality of images, one or more attachments on the patient's dentition;

assigning, based on the plurality of images, each of the one or more attachments to one of the individual teeth depicted in the plurality of images;

identifying a first plurality of the plurality of images in which a first tooth of the individual teeth is visible;

combining the assignments of each of the plurality of images for attachment detection results; and determining that an expected attachment is missing from the first tooth, when, based on the combination of assignments, an attachment is not depicted on the first tooth in a majority of the first plurality of the plurality of images.

2. The system of claim 1, wherein identifying, from the plurality of images, individual teeth of the patient's dentition includes segmenting the individual teeth of the patient's dentition contained in the image.

3. The system of claim 2, wherein segmenting the individual teeth includes determining which teeth are located in the image and which pixels of the image are a part of each tooth.

4. The system of claim 1, wherein the identifying the individual teeth includes assigning each identified tooth to a corresponding tooth in a patient's treatment plan.

5. The system of claim 4, wherein the identifying the individual teeth includes removing a tooth that is not present in the patient's treatment plan.

6. The system of claim 1, wherein the memory storing the instructions that, when executed by the one or more processors, cause the system to perform further operations comprising:

forming a bounding box around each detected attachment.

7. The system of claim 6, wherein assigning each of the one or more attachments to one of the individual teeth includes:

determining a center point of the attachment bounding box; and assigning the attachment to a tooth of the individual teeth based on where the center point is located.

8. The system of claim 6, wherein assigning each of the one or more attachments to one of the individual teeth includes:

determining a center point of the attachment bounding box; and assigning the attachment to a tooth of the individual teeth based on a nearest tooth to where the center point is located.

9. The system of claim 6, wherein assigning each of the one or more attachments to one of the individual teeth includes:

determining an area of each tooth within the bounding box; and assigning the attachment to the tooth based on which tooth has a greatest area within the bounding box.

10. The system of claim 9 wherein assigning the attachment to the tooth is constrained to teeth likely to be in a photo based on a particular view from which the photo is taken.

11. The system of claim 10, wherein in an anterior view the teeth likely to be in the photo are central and lateral incisors and canines.

12. The system of claim 10, wherein in a left lateral view the teeth likely to be in the photo are central incisors, left lateral incisors, left canines, first and second left bicuspids, and first left molars.

13. The system of claim 10, wherein in a right lateral view the teeth likely to be in the photo are central incisors, right lateral incisors, right canines, first and second right bicuspids, and first right molars.

14. The system of claim 6, wherein assigning each of the one or more attachments to one of the individual teeth includes:

determining an amount of overlap of one or more teeth and a vertical mesial edge of the bounding box; and assigning the attachment to a tooth of the one or more teeth with the greatest amount of overlap.

15. The system of claim 1, wherein the memory storing the instructions that, when executed by the one or more processors, cause the system to perform further operations comprising:

determining a number of attachments that should be on each tooth based on the number of attachments placed on each tooth in the patient's treatment plan.

16. The system of claim 1, wherein combining the assignments of each of the plurality of images for attachment detection results includes:

for each image, identifying which teeth can be seen in the image; and determining for each respective tooth, whether or not a single image of the plurality of images depicts an expected number of attachments on the respective tooth.

17. The system of claim 16, wherein the memory storing the instructions that, when executed by the one or more processors, cause the system to perform further operations comprising:

determining that an attachment is missing if a single image depicts less than the expected number of attachments.

18. The system of claim 16, wherein the memory storing the instructions that, when executed by the one or more processors, cause the system to perform further operations comprising:

determining that an attachment is missing if the plurality of images depicts less than the expected number of attachments.

19. The system of claim 1, wherein combining the assignments of each of the plurality of images for attachment detection results includes:

for each image, identifying which teeth can be seen in the image; and determining that an attachment is missing when less than a majority of the plurality of images that depict the tooth also depict an expected number of attachments.

20. The system of claim 1, wherein combining the assignments of each of the plurality of images for attachment detection results includes:

for each image, identifying which teeth can be seen in the image; and determining that an attachment is missing when a majority of the plurality of images that depict the tooth also depict less than an expected number of attachments.

21. The system of claim 1, wherein the plurality of images include images with arches in an open-bite.

22. The system of claim 1, wherein the plurality of images include images with arches in a closed-bite.

23. The system of claim 1, wherein the plurality of images include an anterior image with arches in an open-bite, a left lateral image with the arches in the open-bite, a right lateral image with the arches in the open-bite, an anterior image with the arches in a closed-bite, a left lateral image with the arches in the closed-bite, and a right lateral image with the arches in the closed-bite.

* * * * *